United States Patent
Katwala et al.

(10) Patent No.: US 10,755,804 B2
(45) Date of Patent: Aug. 25, 2020

(54) HEALTH INFORMATION SYSTEM FOR SEARCHING, ANALYZING AND ANNOTATING PATIENT DATA

(71) Applicant: Talix, Inc., San Francisco, CA (US)

(72) Inventors: Niraj Katwala, San Francisco, CA (US); Shahyan Currimbhoy, San Francisco, CA (US); Dean Stephens, San Francisco, CA (US)

(73) Assignee: Talix, Inc., San Francisco, CA (US)

( * ) Notice: Subject to any disclaimer, the term of this patent is extended or adjusted under 35 U.S.C. 154(b) by 547 days.

(21) Appl. No.: 15/645,965

(22) Filed: Jul. 10, 2017

(65) Prior Publication Data

US 2018/0046764 A1 Feb. 15, 2018

Related U.S. Application Data

(60) Provisional application No. 62/372,946, filed on Aug. 10, 2016.

(51) Int. Cl.

| G06F 17/30 | (2006.01) |
|---|---|
| G16H 10/60 | (2018.01) |
| G16H 15/00 | (2018.01) |
| G06F 40/30 | (2020.01) |
| G06F 40/169 | (2020.01) |
| G06F 40/242 | (2020.01) |
| G06F 40/247 | (2020.01) |
| G06F 40/295 | (2020.01) |

(52) U.S. Cl.
CPC .......... *G16H 10/60* (2018.01); *G06F 40/169* (2020.01); *G06F 40/242* (2020.01); *G06F 40/247* (2020.01); *G06F 40/295* (2020.01); *G06F 40/30* (2020.01); *G16H 15/00* (2018.01)

(58) Field of Classification Search
CPC ............................. G16H 10/60; G06F 40/30
See application file for complete search history.

(56) References Cited

U.S. PATENT DOCUMENTS

| 7,512,576 B1 | 3/2009 | Syeda-Mahmood et al. |
|---|---|---|
| 7,853,446 B2 | 12/2010 | Allard et al. |
| 8,108,381 B2 * | 1/2012 | Eberholst ............ G06F 16/3347 707/713 |
| 8,504,392 B2 | 8/2013 | Saria et al. |
| 8,538,915 B2 | 9/2013 | Drissi et al. |
| 8,626,533 B2 | 1/2014 | Rao et al. |
| 8,793,199 B2 | 7/2014 | Syeda-Mahmood et al. |
| 8,805,756 B2 | 8/2014 | Boss et al. |
| 8,903,787 B2 | 12/2014 | Kottaram |
| 9,002,773 B2 | 4/2015 | Bagchi et al. |
| 9,020,810 B2 | 4/2015 | Gliozzo |

(Continued)

FOREIGN PATENT DOCUMENTS

WO 2015/084615 A1 6/2015

*Primary Examiner* — Jeff A Burke
(74) *Attorney, Agent, or Firm* — Ascenda Law Group, PC

(57) ABSTRACT

Disclosed herein are improved systems, methods, and machine readable media for implementing a service for enriching patient documents using natural language processing and a semantic health taxonomy, among other types of information. Enriched documents may be mined for improved diagnostic coding and health services documentation purposes, for example to identify missed and/or inaccurately coded diagnosis codes and quality gaps.

21 Claims, 23 Drawing Sheets

(56) References Cited

U.S. PATENT DOCUMENTS

| | | |
|---|---|---|
| 9,075,796 B2 | 7/2015 | Markatou et al. |
| 9,594,872 B2* | 3/2017 | Masarie, Jr. et al. |
| 9,690,861 B2* | 6/2017 | Boloor ................ G06F 16/9535 |
| 9,785,887 B2* | 10/2017 | Bornea ................ G06F 16/285 |
| 9,792,549 B2* | 10/2017 | Bornea ................ G06F 16/285 |
| 2009/0150183 A1 | 6/2009 | Schmitt et al. |
| 2013/0253949 A1 | 9/2013 | Sethumadhavan et al. |
| 2013/0332187 A1 | 12/2013 | Maman et al. |
| 2014/0122389 A1 | 5/2014 | Riskin |
| 2015/0142473 A1 | 5/2015 | Sethumadhavan et al. |
| 2015/0154362 A1 | 6/2015 | Masarie, Jr. et al. |
| 2015/0178874 A1 | 6/2015 | Harris et al. |
| 2015/0186777 A1 | 7/2015 | Lecue et al. |
| 2015/0317743 A1 | 11/2015 | Flam et al. |
| 2015/0356647 A1 | 12/2015 | Reiser et al. |
| 2016/0019299 A1 | 1/2016 | Boloor et al. |
| 2016/0283656 A1 | 9/2016 | Charlot et al. |
| 2017/0193185 A1* | 7/2017 | Barker .................. G06F 16/285 |
| 2018/0032679 A1* | 2/2018 | Dandala .................. G06F 16/26 |
| 2018/0068076 A1* | 3/2018 | Farri .................... G06F 19/324 |
| 2018/0226141 A1* | 8/2018 | Slepian .................. G06Q 10/06 |
| 2018/0260426 A1* | 9/2018 | Sharifi Sedeh ....... G06F 19/326 |
| 2019/0013093 A1* | 1/2019 | Slepian .................. G06N 5/046 |

* cited by examiner

FIG. 9

Patient 1 — DOB: Mar 1941  Age: 75  Gender: Male  Physician: Physician 1  CID: 6127  MRN: 2ACFACEC-A73D-48D8-B17A-22F847A1042E — 900

Back  Reset  Plan Year: 2016

Coding Opportunities | HCC Summary | Activity Log | Encounter View | Opportunity View Encounter: (7) Jan 1, 2016  Open Opportunities: 7 — 902
☐ HCC  ☐ Additional Evidence

| Patient Plan | DOS: Dec 23, 2014 | a8fba281-e692-4bc2-89f3-70fb119b9efc.doc | | | |
|---|---|---|---|---|---|
| Completed Orders (this encounter) | | | | | |
| Order | Details | Reason | Side | Interpretation | Result |
| PT INR (in House) | | | | normal | PT-31.0 Mary Jackson... |
| PROTHROMBIN TIME | | | | | |

Assessment / Plan     Document: 1 | 2 | 3 | 4 | 5 | 6 — 903

| # | Detail Type | Description |
|---|---|---|
| 1. | Assessment | Long-term Use of Anticoagulants (V58.61). |
| | Patient Plan | Continue current rx., follow up 1 month. |
| | Plan Orders | The patient had the following test(s) completed today PT INR (in House)... |
| 2. | Assessment | Foot ulceration (707.15). |
| | Patient Plan | Follow up Podidtry, will check lab, may need arteriogram in the future. |
| 3. | Assessment | Atrial fibrillation (427.31). |
| | Plan Orders | Mary Jackson Comprehensive Metabolic Panel, Hemoglobin A1c with eAG Lipid Panel and Venipuncture_IH to be performed. |
| 4. | Assessment | Parkinson's Disease (332.0). — 908a |
| 5. | Assessment | Bipolar I disorder, most recent episode (or current) unspecified (296.7). |
| 6. | Assessment | Major depressive affective disorder, single episode, unspecified degree... |
| 7. | Assessment | Chronic airway obstruction, not elsewhere classified (496). |

Sort by RAF adjustment  — 904

| | | HCC | Status |
|---|---|---|---|
| Current: | 906a | 0.691 | ● accept |
| Proposed: | G20: Parkinson's Disease | | ○ reject |
| Proposed: | | | ○ review |
| Additional notes | | | |
| Additional evidence: | | | ⟨ ⟩ |
| Suspected: | I69.949 - Monoplegia... | 0.396 | tentative |
| Suspected: | E10.618 - Type 1 dia... | 0.368 | tentative |
| Suspected: | E11.618 - Type 2 dia... | 0.368 | tentative |
| Suspected: | I50.9 - Cardiac Failure | 0.346 | accept |
| Suspected: | I44.9 - Chronic Obstr... | 0.330 | review |
| Suspected: | F31.9 - Bipolar Disord... | 0.295 | tentative |
| Suspected: | I48.91 - Unspecified... | 0.396 | tentative |
| Suspected: | I69.949 - Monoplegia... | 0.141 | tentative |
| Suspected: | I20.8 - Other forms of... | | |

Patient 1

DOB: Mar 1941  Age: 75  Gender: Male  Physician: Physician 1  CID: 6127  MRN: 2ACFACEC-A73D-48D8-B17A-22F847A1042E  Plan Year: 2016

Coding Opportunities | HCC Summary | Activity Log

Encounter: (6) Jan 1, 2016  Open Opportunities: 6
☐ HCC  ☐ Additional Evidence

Encounter View | Opportunity View — 900 nurse master  DOS: May 7, 2014  a8fba281-e692-4bc2-89f3-70fb119b9efc.doc
Document 1|2|3|4|5|6 — 902
903 — ↗
904 — ↗

PATIENT: Patient 1
DATE OF BIRTH: 03/ /1941
DATE: 05/07/2014 2:10 PM
VISIT TYPE: Office Visit History of Present Illness
This 73 year old man presents with:
1. chronic conditions
Chronic Conditions
Congestive heart failure
Other and unspecified angina pectoris
Bipolar I disorder, most recent episode (or current)
Atrial fibrillation
Hypoxemia
Chronic kidney disease, Stage III (moderate)
COPD
Long-term Use of Anticoagulants
Left Great Toe Amputation
Parkinson's Disease

| Sort by RAF adjustment ⇅ | | HCC | Status |
|---|---|---|---|
| Current: | 906b | 0.779 | accept |
| Proposed: | Z89.419 Acquired absence of unspecified ... ⇅ | | ● accept<br>○ reject<br>○ review |
| Comments: | | | |
| Additional notes | | | |
| Additional evidence: | | | |
| ⊕ | | | ◁ ▷ |
| Suspected: | I69.949 - Monoplegia.. | 0.396 | tentative |
| Suspected: | E10.618 - Type 1 dia.. | 0.368 | tentative |
| Suspected: | E11.618 - Type 2 dia.. | 0.368 | tentative |
| Suspected: | I50.9 - Cardiac Failure | 0.368 | accept |
| Suspected: | I44.9 - Chronic Obstr.. | 0.346 | review |
| Suspected: | F31.9 - Bipolar Disord.. | 0.330 | tentative |
| Suspected: | I48.91 - Unspecified... | 0.295 | tentative |
| Suspected: | I69.949 - Monoplegia.. | 0.396 | tentative |
| Suspected: | I20.8 - Other forms of.. | 0.141 | tentative |

FIG. 11

Back | > | Patient 1 | CID: 6127 | MRN: 2ACFACEC-A73D-48D8-B17A-22F847A1042E
DOB: Mar 1941 Age: 75 Gender: Male Physician: Physician 1 | Reset | Plan Year: 2016

Coding Opportunities | HCC Summary | Activity Log | Encounter View | Opportunity View Encounter: (6) Jan 1, 2016 ⊕ Open Opportunities: 6 — 902
☐ HCC ☐ Additional Evidence Document [1] 2 | 3 | 4 | 5 | 6 — 903 nurse_master  DOS: May 7, 2014  a8fba281-e692-4bc2-89f3-70fb119b9efc.doc

— 908b
Left Great Toe Amputation
Parkinson's Disease
Insomnia, Other
Insulin Dependent Diabetic
Dementia
Major depressive affective disorder, single episode Vital Signs
Unable to obtain weight.

Height:
| Time | ft | in | cm | Last Measured | Method | % | Measured By |
|---|---|---|---|---|---|---|---|
| 2:30 PM | 0.0 | 0.00 | 0.00 | 05/07/2014 | carried forward | | Medical Professional 1 |

Blood Pressure:
| Time | BP mm/Hg | Position | Side | Site | Method | Cuff Size | Measured By |
|---|---|---|---|---|---|---|---|
| 2:30 PM | 109/62 | sitting | | | | | Medical Professional 1 |

Temperature/Pulse/Respiration
| Time | Temp F | Temp C | Temp Site | Pulse/min | Pattern | Resp/min | Measured By |
|---|---|---|---|---|---|---|---|
| 2:30 PM | 97.4 | | | | | | Medical Professional 1 |

Medications
| Started | Medication | Directions | Comment | Stopped |
|---|---|---|---|---|
| 03/28/2014 | Aricept 10 mg tablet | take 2 Tablet by oral route every day in the evening | | |
| 11/22/2013 | Coreg 3.125 mg ... | take 1 Tablet (3.125mg) by | | |

Sort by RAF adjustment ⊕ | | HCC | Status
Current: | 906b | 0.779 | accept
Proposed: Z89.419 Acquired absence of unspecified ... ⊕
⊙ accept  ○ reject  ○ review
Comments: ⊕

Additional notes

Additional evidence: — 1202
⊙ Left Great Toe Amputation
⊕ | < | >

Suspected: 169.949 - Monoplegia.. | 0.396 | tentative
Suspected: E10.618 - Type 1 dia.. | 0.368 | tentative
Suspected: E11.618 - Type 2 dia.. | 0.368 | tentative
Suspected: 150.9 - Cardiac Failure | 0.346 | accept
Suspected: 144.9 - Chronic Obstr.. | 0.330 | review
Suspected: F31.9 - Bipolar Disord.. | 0.295 | tentative
Suspected: 148.91 - Unspecified... | 0.396 | tentative
Suspected: 169.949 - Monoplegia.. | 0.141 | tentative
Suspected: 120.8 - Other forms of..

← Back | Patient 1 | DOB: Mar 1941 Age: 75 Gender: Male | Physician: Physician 1 | Plan Year: 2016 ▾

CID: 6127  MRN: 2ACFACEC-A73D-48D8-B17A-22F847A1042E

↗ 1300

Reset

| Coding Opportunities | HCC Summary | Activity Log | | Encounter View | Opportunity View |

← 904    ← 903    ← 902

☐ HCC  ☐ Additional Evidence    [Detach] Jan 1, 2016

Document: 1 [2]    a8fba281-e692-4bc2-89f3-70fb119b9efc.doc nurse_master

Lab Requisition

Patient Name: Patient 1
Address: 1111 Streetname St.
Houston TX 77043
Date of Birth: 03/ /1941

Diagnosis: Dx Code:
1. Long-term Use of Anticoagulants (V58.61)
2. COPD (496)
3. Parkinson's Disease      (332.0)
4. Insomnia, Other (780.52)
5. Insulin Department Diabetic (250.01)
6. Left Great Toe Amputation [V49.71] ← 908c
7. Dementia (294.20)
8. Major depressive affective disorder, single episode (296.20)

Ordered by:  Physician 1  MD
Date: 01/06/2014 3:00 PM

Provider:  Physician 1   01/06/2014
Doe Medical Center

Document generated by:  Physician 1   01/06/2014

---

Sort by RAF adjustment ▾ | HCC | Status

Current:
Proposed: Z89.419 Acquired absence of unspecified ... ▾ | 0.779 | accept Comments: | ● accept  ○ reject  ○ review Additional notes Additional evidence:
⊖ Left Great Toe Amputation
⊕

◁ ▷

| Suspected: 169.949 - Monoplegia.. | 0.396 | tentative |
| Suspected: E10.618 - Type 1 dia... | 0.368 | tentative |
| Suspected: E11.618 - Type 2 dia... | 0.368 | tentative |
| Suspected: 150.9 - Cardiac Failure | 0.368 | accept |
| Suspected: 144.9 - Chronic Obstr... | 0.346 | review |
| Suspected: F31.9 - Bipolar Disord... | 0.330 | tentative |
| Suspected: 148.91 - Unspecified... | 0.295 | tentative |
| Suspected: 169.949 - Monoplegia.. | 0.396 | tentative |
| Suspected: 120.8 - Other forms of.. | 0.141 | tentative |

FIG. 15

Back | Patient 1

DOB: Mar 1941  Age: 75  Gender: Male  Physician: Physician 1  CID: 6127  MRN: 2ACFACEC-A73D-48D8-B17A-22F847A1042E  Reset Coding Opportunities | HCC Summary | Activity Log Year: ◉ 2015 ▼ | Disability Status: not disabled | Demographics Score (HCC): 0.421 ←1507                                                                         ←1500

←1502              ←1504                                                                                                                                        ←1506

| ICD | ICD Description | HCC | HCC Description | Last Payment Date ▲ | Date of Service | Coded Plan Year | Risk Score |
|---|---|---|---|---|---|---|---|
| 296.20 | Major depressive affective disorder, single episode, unspecified | 58 | Major Depressive, Bipolar, and Paranoid Disorders | 23-Mar-15 | 18-Mar-15 | 2014 | 0.33 |
|  |  | 55 | Major Depressive, Bipolar, and Paranoid Disorders |  |  | 2015 | 0.36 |
| 296.7 | Bipolar I disorder, most recent episode (or current) unspecified | 58 | Major Depressive, Bipolar, and Paranoid Disorders | 14-May-15 | 08-May-15 | 2014 | 0.33 |
|  |  | 55 | Major Depressive, Bipolar, and Paranoid Disorders |  |  | 2015 | 0.36 |
| 250.01 | Diabetes mellitus without mention of complication, type I [juvenile type], not stated as uncontrolled | 19 | Diabetes without Complications | 10-Jul-15 | 07-Jul-15 | 2014 | 0.118 |
| 332.0 | Paralysis agitans | 78 | Parkinson's and Huntington's Diseases | 10-Jul-15 | 07-Jul-15 | 2014 | 0.691 |
|  |  | 73 | Parkinson's and Huntington's Diseases |  |  | 2015 | 0.643 |
| 428.0 | Congestive heart failure, unspecified | 85 | Congestive Heart Failure | 10-Jul-15 | 07-Jul-15 | 2014 | 0.368 |
|  |  | 80 | Congestive Heart Failure |  |  | 2015 | 0.346 |
| 427.31 | Atrial fibrillation | 96 | Specified Heart Arrhythmias | 10-Jul-15 | 07-Jul-15 | 2014 | 0.295 |
|  |  | 92 | Specified Heart Arrhythmias |  |  | 2015 | 0.289 |
| V49.71 | Great toe amputation status | 189 | Amputation Status, Lower Limb / Amputation Complications | 10-Jul-15 | 07-Jul-15 | 2014 | 0.779 |
|  |  | 177 | Amputation Status, Lower Limb / Amputation Complications |  |  | 2015 | 0.793 |

←1508

| Interaction Factor (HCC) | Code 1 | Code 2 | Factor |
|---|---|---|---|
|  | 250.01 | 428.0 | 0.182 |

| DOB: Mar 1941 | Age: 75 | Gender: Male | Physician: Physician 1 | | Patient 1 | CID: 6127 | MRN: 2ACFACEC-A73D-48D8-B17A-22F847A1042E | Plan Year: 2016 |
|---|---|---|---|---|---|---|---|---|
| Coding Opportunities | HCC Summary | | Activity Log | | | | | |
| Date Of Action ▼ | Date Of Service | User | Action | Code | Notes | | | Evidence |
| 25-May-2016 | 01-Jan-2016 | hatkin | accept | 150.9 | | | | Show evidence.. |
| 25-May-2016 | 01-Jan-2016 | hatkin | review | J44.9 | | | | Show evidence.. |
| 25-May-2016 | 01-Jan-2016 | hatkin | review | J44.9 | COPD may be less likely | | | Show evidence.. |
| 25-May-2016 | 01-Jan-2016 | hatkin | review | J44.9 | COPD may be less likely in absence of smoking | | | Show evidence.. |
| 25-May-2016 | 01-Jan-2016 | hatkin | accept | G20 | | | | Show evidence.. |
| 25-May-2016 | 01-Jan-2016 | hatkin | accept | Z89.419 | | | | Show evidence.. |
| 25-May-2016 | 01-Jan-2016 | hatkin | tentative | 120.8 | | | | Show evidence.. |

FIG. 16

HEALTH INFORMATION SYSTEM FOR SEARCHING, ANALYZING AND ANNOTATING PATIENT DATA

RELATED APPLICATIONS

The present invention claims the priority benefit of U.S. Provisional Patent Application No. 62/372,946, filed on Aug. 10, 2016, the disclosure of which is incorporated herein by reference in its entirety.

FIELD OF THE INVENTION

The present invention relates to improved apparatuses, systems, computer readable media, and methods for the provision of services concerning semantic annotation, enrichment, and searching of patient data.

BACKGROUND

Accurate diagnoses and information about patient health can be lost in the large volume of structured and unstructured data that document a patient's health history. There is a need for improved systems for understanding the content of that volume of data and mining it for actionable information in order to improve the accuracy and efficiency of identifying patient medical acuity, treatments and health management and associated record-keeping. Disclosed herein are embodiments of an invention that address those needs.

BRIEF DESCRIPTION OF THE DRAWINGS

The above and other aspects and advantages of the invention will become more apparent upon consideration of the following detailed description, taken in conjunction with the accompanying drawings, in which like reference characters refer to like parts throughout, and in which:

FIG. 9 shows an exemplary user interface for documenting health services, consistent with some embodiments of the invention;

FIG. 10 shows an exemplary user interface for documenting health services, consistent with some embodiments of the invention;

FIG. 11 shows an exemplary user interface for documenting health services, consistent with some embodiments of the invention;

FIG. 12 shows an exemplary user interface for documenting health services, consistent with some embodiments of the invention;

FIG. 13 shows an exemplary user interface for documenting health services, consistent with some embodiments of the invention;

FIG. 14 shows an exemplary user interface for documenting health services, consistent with some embodiments of the invention;

FIG. 15 shows an exemplary user interface for documenting health services, consistent with some embodiments of the invention;

FIG. 16 shows an exemplary user interface for documenting health services, consistent with some embodiments of the invention;

DETAILED DESCRIPTION

Figure 1A:
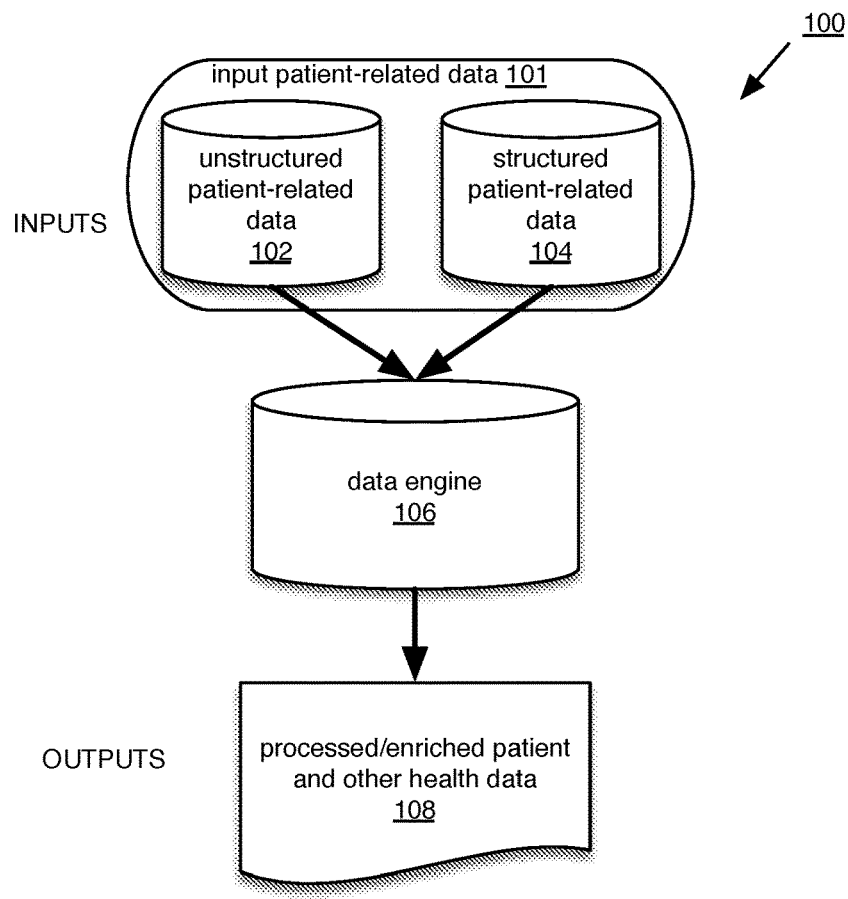
FIG. 1A and FIG. 1B show an overview of a data enrichment process, consistent with some embodiments of the invention.

Disclosed herein are systems, methods, and machine readable media for implementing a service for enriching patient-related data. In one aspect, the invention involves one or more memories configured to implement an improved application of natural language processing to enable deep-mining of the patient data. Thus, embodiments of the invention provide improvements in computer-related technology through techniques for enabling more accurate and comprehensive extraction of health-related concepts. These concepts are supported or suggested by textual or quantitative evidence embedded in one or more documents comprising a patient's medical record and associated information about the patient. For example, enriching patient data and documents using a semantic taxonomy permits improved, automated, natural language processing of documents and fields within documents containing unstructured text for more accurate and complete detection of health and patient-related concepts; the identified concepts may then be used for further application of automated techniques to improve the detection of patient health problems (e.g., automatic identification of potential complex health disorders such as irritable bowel syndrome and/or health conditions such as congestive heart failure) and accounting issues (e.g., automatic review of documentation of health services for purposes of insurance claims verification). Use of automated word-sense disambiguation and coordinate expansion corrects notorious sources of errors in natural language processing, enhancing the accuracy of the detection of health and patient-related concepts. Use of nuanced scaling for components of a document-concept ranking procedure as described herein improves the accuracy of processing and scope of the unstructured input that can be handled by the enrichment approach. The specific use of a stack or tiers of annotators described herein additionally improves accuracy and coverage of identifying and extracting instances of entities.

Embodiments of the invention further include improved techniques for annotating and searching patient data using clinical guidelines, which may involve the application of both natural language understanding to identify qualitative concepts or other entities and quantitative measurements that are present in structured and unstructured data, as well as the intelligent application of rules based on the clinical guidelines.

Embodiments of the invention further include automatically inferring proposed medical codes and quality care gaps supported by concepts identified in the patient data, for example in accordance with the service for enriching patient-related data. One aspect of this improved service is that the proposed codes (or predicted conditions) may incorporate evidence from multiple documents that can be associated with the patient, and thus the proposed codes may provide a more accurate assessment of a patient's condition or medical acuity compared to proposed codes that are limited to analysis of a single document at a time. A series of user interfaces for reviewing proposed codes in the context of documenting health services and conditions is also provided. In certain embodiments, the user interfaces provide proposed codes along with estimates for how confirming the codes affect an assessment of the level of risk associated with that patient (e.g., a "risk adjustment factor", RAF), as well as the overall risk assessment for populations containing that patient. In certain embodiments, the RAF is continuously updated and provided for each patient as additional data is incorporated into the system (e.g., updates to electronic medical records, medical claims, laboratory test results, radiology reports, medical voice to text transcription, and the like). By continually identifying proposed codes and related RAFs, a patient's otherwise neglected health issues may be addressed closer in time to when issues arise or are identified, rather than after a retrospective analysis when the patient may be sicker because a health issue has been neglected for a longer period of time.

Embodiments of the invention further include proposing health-related services based on information about the patient identified in patient data, including, for example, recommended post-hospital services, medications, physician documentation at patient encounter or tests based on socioeconomic factors and identified care needs.

As used herein, a "patient" refers to an individual who may receive or have received medical services. Depending on the context, a "user" may be an administrator or health professional who is accessing or editing information about one or more patients. In certain contexts or embodiments, a "user" may also be a patient. In certain contexts or embodiments, a "user" may be a developer or curator involved with creation or maintenance of a data engine as described below FIG. 1 shows an overview of a data enrichment process, consistent with some embodiments of the invention. FIG. 1A shows a process 100 in which unstructured patient-related data 102 and structured patient-related data 104 (collectively, input patient-related data 101) are inputs to data engine 106, which is used to generate processed and enriched patient-related data 108 based on the input data. Patient-related data 101 and 108 may comprise documents. Structured data 104 is data that adheres to a regular or defined format, so that information categories and values may be more easily extracted using an automated parser. Unstructured data 102 does not have a defined format, and may constitute, for example, free text. Certain documents may involve a combination of structured and unstructured data—for example, a structured document that includes short defined fields and some lengthy text fields, e.g., a comment field. Unstructured patient-related data 102 may include, for example, treatment authorization requests. Structured patient-related data 104 may include, for example, electronic medical record (EMR) data, formulary lists of drugs. Input patient-related data 101 may include, for example, insurance claim documents, prescription systems data, laboratory results, radiology results, and social network data.

Figure 1B:
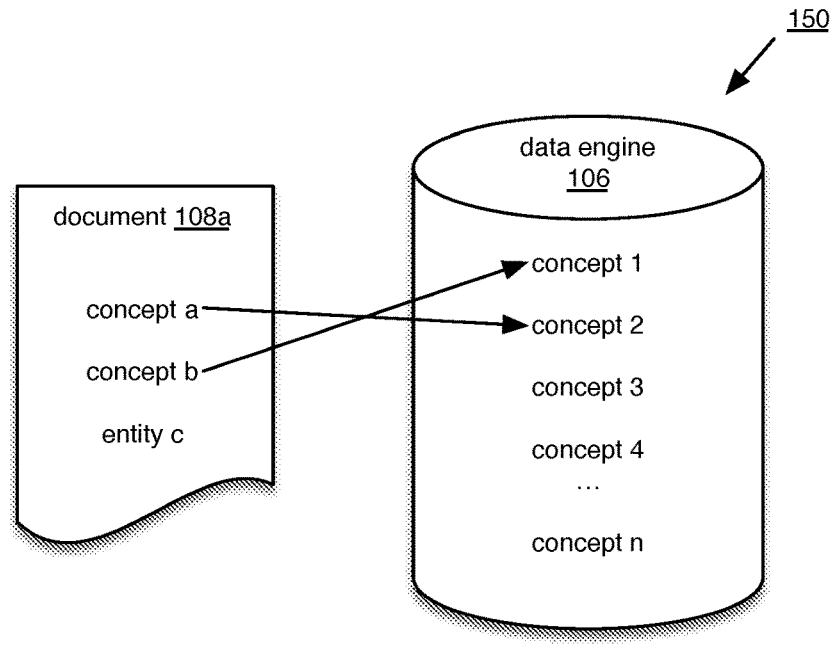

FIG. 1B shows an example 150 in which exemplary enriched patient document 108a has been enriched by associating instances of its constituent entities with concepts in data engine 106. As used herein, a "concept" refers to a term or an idea in a semantic taxonomy and is associated with a list of clinical attributes such as synonyms, abbreviations, acronyms and medical codes. An "entity" refers to a thing that may be expressed in text (e.g., associated with a text token or a diagnostic textual pattern). The category of entities includes concepts. Instances of entities (including instances of concepts) may be found in a document or other data, such as an input patient-related data 101. Examples of concepts include cancer, aspirin, and lung. Examples of entities that are not clinical concepts include a date of birth or a social security number. In certain embodiments, some concept instances may represent concepts that are not present in an exemplary semantic taxonomy—for example, the instance may correspond to an entity that is an entry in a separate dictionary (in which the entry/concept may be represented in the dictionary as a term and its definition), or may represent a concept instance that could be added to a semantic taxonomy or dictionary. A "semantic taxonomy" refers to a collection of concepts and their interrelationships. For example, the text "diabetic retinopathy" and "acanthosis nigricans" found in an input document 102a may be identified as instances of the concepts "diabetic retinopathy" and "acanthosis nigricans." The corresponding concepts in data engine 106 may be further associated with the concept "Type II Diabetes," as the two conditions are clinically associated with Type II Diabetes. This relationship may cause the inferred entity "Type II Diabetes" to be associated with document 102a as well. In certain embodiments, the text relating to the first two conditions are present in separate input documents associated with the same patient, and data engine 106 infers the third condition across documents to associate "Type II Diabetes" with the patient. Thus one aspect of enriching input data is to identify instances that are suggested or present in the input data, and link those instances with the corresponding concepts in a semantic taxonomy or other defined entities (e.g., creating an entity link). An entity link associates a patient document, patient data, a portion of a patient document, or evidence extracted from a patient document with a concept or other entity. In FIG. 1B, data engine 106 comprises a semantic taxonomy that includes concepts 1-n. A more specific example of concepts in a semantic taxonomy is provided in FIG. 3. Because the concepts in a semantic taxonomy may be associated with additional attributes and interrelationships, associating concept instances in document 108a with the concepts in data engine 106 may enable automatic inferences, searching, and mining of the patient data that are unavailable using the raw input data. For example, the enriched data may be searchable across large bodies of content, using a natural language search; patients may be grouped into cohorts based on key attributes or factors, and treatment authorization requests may be matched to clinical policy bulletins.

In addition to associating constituent instances with concepts and other entities, enrichment of patient-related data may include, for example, normalization of values such as measurements, and annotation of documents using clinical rules and other types of rules. In certain embodiments, the enriched document 108 maintains a respective reference to the evidence in the original input data document 101 that supports each identified entity/concept. In certain embodiments, the enriched data 108 is the original document 102 or 104 along with additional metadata identifying linked concepts and other annotations.

Figure 2:
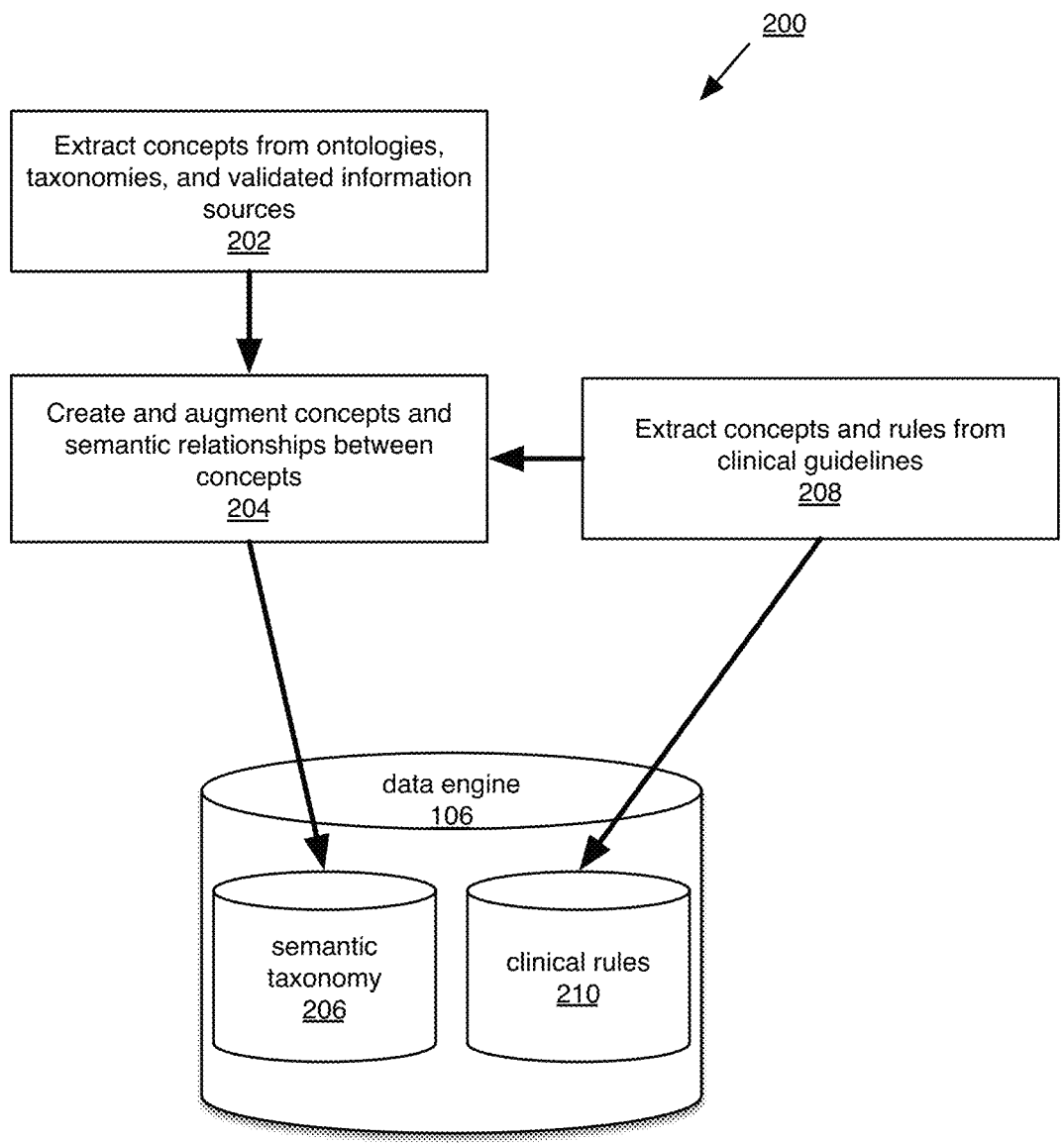
FIG. 2 shows an overview of a process for building a data engine, consistent with some embodiments of the invention.

FIG. 2 shows an overview of an exemplary process 200 for building a data engine 106, consistent with some embodiments of the invention.

In step 202, candidate concepts are extracted from preexisting ontologies, taxonomies, and validated information sources that define or manage controlled terminologies and codes. For example, concepts may be obtained from the National Cancer Institute Thesaurus (NCI-T), the Healthcare Common Procedure Coding System (HCPCS), International Classification of Diseases (e.g., ICD-9, ICD-10), Gene Ontology (GO) project, the Systematized Nomenclature of Medicine (SNOMED), Online Mendelian Inheritance in Man (OMIM), National Drug Code (NDC), Current Procedure Terminology codes (e.g., CPT-4), Logical Observation Identifiers Names and Codes (LOINC), National Library of Medicine (NLM) Medical Subject Headings (MeSH), Diagnosis-Related Group (DRG) codes, and NLM RxNorm.

In step 204, the candidate concepts are used to define, augment, and correct concepts and relationships between concepts in a semantic taxonomy 206. This step may involve, for example, automatic identification or human curation of semantic relationships between concepts, creation of consumer friendly names, performing clinical quality control, defining synonyms, acronyms and abbreviations for concepts and attributes, creating stemming and correction lists (e.g., equating inject/injects/injecting where appropriate, and defining common misspellings of words), handling same-spelling homonyms and phrases involving negation, and defining term- and query-specific rules. In certain embodiments, step 204 may involve automatically identifying or suggesting concepts through data mining of published clinical/scientific literature, or human curation using clinical/scientific literature. In certain embodiments, step 204 may involve incorporating organization-specific terminologies into the semantic taxonomy 206. In certain embodiments, sets of concepts may constitute individual databases within the semantic taxonomy 206. Augmenting concepts and relationships may involve associating categories or labels and associated values for attributes of concepts and concept relationships.

In certain embodiments, a terminology editor provides a user interface for facilitating one or more aspects of step 204 (e.g., human curation of concepts).

In step 208, a set of clinical rules 210 may be incorporated into data engine 106. This may involve, for example, extracting clinical rules from clinical rules input documents such as existing published clinical guidelines, organization-specific clinical guidelines, clinical policy bulletins, or published scientific and clinical literature including books and journals. Concepts in the semantic taxonomy 206 that are implicated by particular clinical rules may be associated with those rules within data engine 106. Defining new clinical rules may involve creating or augmenting such concepts as in step 204. In certain embodiments, data engine 106 may additionally include predefined collections of entities that are not concepts (e.g., dictionaries of entities).

In certain embodiments, a clinical guidelines editor provides a user interface for facilitating aspects of step 208 (e.g., creating a machine-readable clinical guideline from a clinical rules input document). In certain embodiments, creation of new clinical rules from clinical rules input documents is automated.

Figure 3:
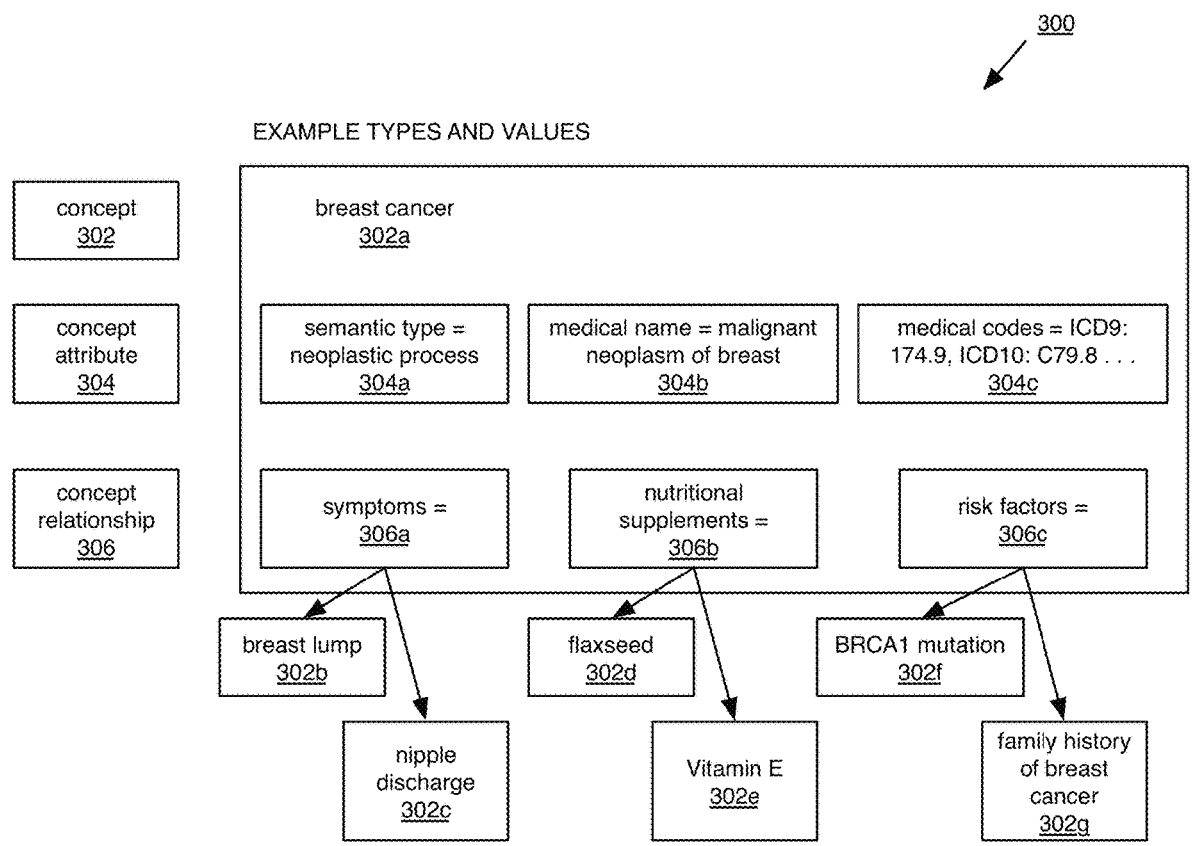
FIG. 3 shows an exemplary portion of a semantic taxonomy, consistent with some embodiments of the invention.

FIG. 3 shows an exemplary portion of a semantic taxonomy 300, consistent with some embodiments of the invention. A semantic taxonomy (such as taxonomy 206) contains a plurality of concepts 302. Each concept 302 is associated with one or more concept attributes 304. Each concept attribute 304 has a type or label and one or more values. For example, in FIG. 3, example concept "breast cancer" 302a has at least three concept attributes, 304a-304c. Concept attribute 304a has type "semantic type" and value "neoplastic process." Concepts 302 may additionally be associated with concept relationships 306 that define how one concept is related to another, e.g., as a symptom, nutritional supplement, or medication related to the neoplastic process "breast cancer," in taxonomy portion 300. In certain embodiments, all concepts 302 of the semantic taxonomy 206 include at least a "semantic type" concept attribute 304. An attribute such as a "semantic type" attribute may permit a taxonomy to have a semantic dimension by defining the semantic character of the associated entity. Thus, in certain embodiments, each concept relationship 306 has a type that may be the value of the "semantic type" concept attribute 304 of a concept 302 (e.g., concept 302d "flaxseed" has attribute 304 type "semantic type" with value "nutritional supplement"), and each relationship 306 has one or more values that identify one or more other concepts 302 (e.g., concept relationship 306b, "nutritional supplements," is associated with concepts 302d and 302e, and concept relationship 306c, "risk factors," is associated with concepts 302f and 302g).

Examples of concept attributes 304 may include semantic type, medical name, medical codes, and synonyms. Medical codes may be defined to be a specific type of code, for example, an ICD-9, ICD-10, RxNorm, or CPT-4 code.

Examples of concept relationship 306 types (e.g., concept semantic types) may include, for example, symptoms, nutritional supplements, medications (e.g., concept: Doxorubicin), complications (e.g., concept: metastatic cancer), therapies, synonyms, preventions (e.g. concepts: breast feeding, low-fat diet), risk factors, physician specialties, treatments (e.g., concepts: chemotherapy, mastectomy), diagnostic procedures (e.g., concept: mammography), neoplastic processes.

Figure 4:
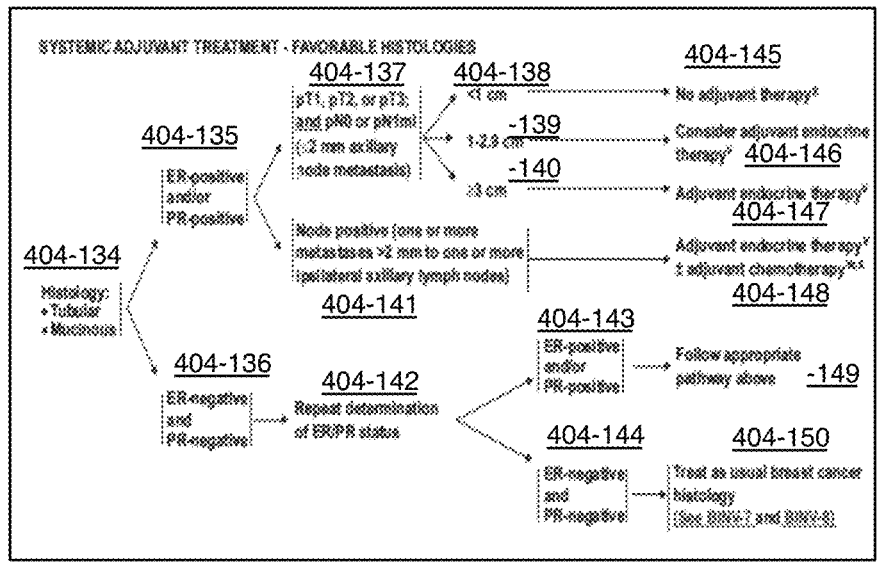
FIG. 4 shows an example diagram concerning a process for creating a machine-readable clinical guideline, consistent with some embodiments of the invention.

FIG. 4 shows an example diagram concerning a process for creating a machine-readable clinical guideline 406. A clinical guideline may be published in a graphical/pictorial format as a pictorial diagram 402, for example as shown in exemplary input pictorial diagram clinical guideline 402a, which is a decision tree as represented in a diagram on a page in a document. In order to use clinical guidelines in embodiments of the invention (e.g., as stored in data engine 106 and clinical rules 210), the input clinical guideline 402, which comprises pictorial clinical rules 404, may be converted to a machine-readable guideline 406. Machine-readable guidelines may be represented as nodes in a graph or decision tree, in which the graph or decision tree represents the overall guideline 406 and where each node 408 comprises a particular clinical rule or step in the decision tree. For example, pictorial clinical rule 404-134 (reading "Histology: *Tubular*Mucinous") indicates that if a tumor is associated with tubular or mucinous histology, the immediately subsequent clinical rules in input clinical guideline 402 apply. (Subsequent clinical rules may be indicated using arrows, such as the arrows extending from rules 404-134 to 404-135 and -136 in FIG. 4.) Clinical rules may be qualitative (for example, a binary test for whether a concept is present) or quantitative (i.e., involving a numerical computation—for example, a test based on evaluating a numerical expression using a value as one or more parameters in the expression). For example, qualitative pictorial clinical rule 404-134 may be represented in node 408-134 as a clinical rule representing the test for whether one or both of the tubular or mucinous histology concepts are associated with a document or patient data, such as input patient-related data 101, where the rule is satisfied or returns True if either concept is present. Quantitative clinical rule 404-138 indicates that if the tumor is less than 1 cm in size, the immediately subsequent clinical rules in input clinical guideline 402a apply. In certain embodiments, nodes 408 may have attributes such as a node rule (e.g., "ER negative and PR negative" for node 408-136) and a node state indicating what the node rule is applied to (e.g., "Hormone receptor status" for node 408-136).

Creation of a machine-readable guideline 406 may involve converting a decision tree represented visually (as in exemplary pictorial guideline 402a) by configuring one or more memories to represent the guideline using a corresponding decision tree or graph data structure (e.g., a data structure including aspects of the node listing in exemplary machine-readable guideline 406a). In certain embodiments, an input guideline 402 may be described in text rather than images or diagrams. In certain embodiments, optical character recognition may be used to automatically extract text associated with an input guideline 402. In certain embodiments, machine learning techniques may be used to automatically identify the sequence of clinical rules represented in a pictorial input guideline. In certain embodiments, aspects of this conversion process may be accomplished via a clinical guidelines editor that provides a user interface (e.g., for human curation of clinical guidelines and clinical rules). In certain embodiments, clinical guidelines may be sourced from the National Guideline Clearinghouse, www.guideline.gov, or a professional medical association for a particular medical specialty or practice area, such as the American Academy of Pediatric Dentistry or the American College of Radiology.

In certain embodiments, the result of evaluating a particular clinical rule or a guideline in regards to data such as a document or patient data 101 is that the data is enriched by associating it with a concept, tag, value, or other information indicating the result of the particular clinical rule (in the case of applying a single clinical rule), or the results of one or more constituent clinical rules (in the case of applying a guideline). In certain embodiments, the input data are associated with these additional concepts, tags, values, or other information in the same manner that entities identified in input data are linked with corresponding concepts in a semantic taxonomy. For example, in certain embodiments, a particular patient document such as a pathology report may provide evidence for deciding that a tumor with tubular histology (a result of rule 404-134) that is also ER-positive (a result of rule 404-135), and is staged as pT2 and pN1mi (a result of rule 404-137), and the tumor is >3 cm (a result of rule 404-140). Based on this evidence, data engine 106 may infer that adjuvant endocrine therapy is recommended (a result of rule 404-147), even if the pathology report does not state or otherwise suggest that "adjuvant endocrine therapy" is recommended or prescribed. In certain embodiments, this inference regarding endocrine therapy may be associated with the patient or the pathology report document along with information regarding the basis for the inference, such as "automatic inference based on clinical guideline <402a>" and a reference to the evidence underlying clinical rules 404-134, 404-135, 404-137 and 404-140. In certain embodiments, an evaluation of the confidence in the result of any individual clinical rule or overall clinical guideline (e.g., a statistical evaluation of the quality of the evidence or the inference based on the guideline) may be associated with the patient or the pathology report document.

Figure 5:
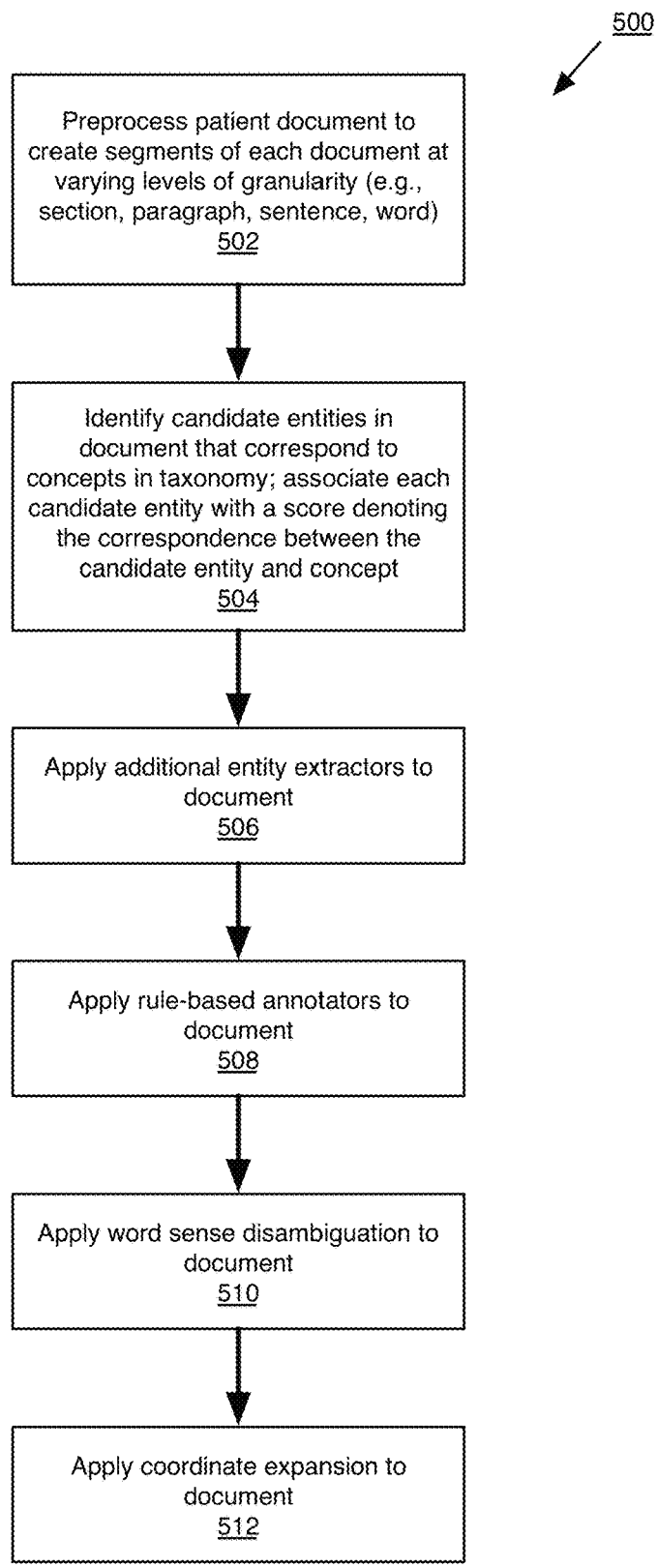
FIG. 5 shows a data enrichment process, consistent with some embodiments of the invention.

FIG. 5 shows an exemplary data enrichment process 500 for enriching data, such as input patient-related data 101, using a data engine to implement the steps, such as data engine 106, resulting in enriched data, such as enriched patient-related data 108. In step 502, input data, such as documents associated with particular patients, is processed to create segments of each document at varying levels of granularity. Segments may be, for example, an entire document, section, paragraph, sentence; one, two, three, or four words; and the like. Segments may further be a number of sentences or a number of words (e.g., four words, or "tokens"). Segments may alternatively be referred to as "views" of the document. For example, each document may be imported into a data structure in which the name of the document, the type of the document, and other information may be retrieved. The data structure may provide access to one or more segments of the documents, and may further associate labels with the segments, e.g. section labels such as "family history" or "vital signs." The data structure may provide access to a list of the document's text broken up into segments, such that each element of the list is a single segment, or such that each element of the list is an identifier or reference to a single segment. In certain embodiments, the data structure may provide access to images and graphical material from the documents. In certain embodiments, prior to step 502, documents may be processed using optical character recognition to extract text from images or scans of paper documents, or voice recordings may be automatically transcribed to text.

In step 504, candidate concept instances are identified in each document that correspond to concepts in a taxonomy, such as semantic taxonomy 206. For example, concept instances may be identified by searching a graphical representation of the taxonomy using the segments. For example, the semantic taxonomy may contain concepts 302 having a concept attribute 304 of type "synonyms," which may include synonyms, abbreviations, and acronyms (or these may be separate attributes). Thus a search of the semantic taxonomy using candidate instance/segments "M.I." or "heart attack" may result in the association of a concept "myocardial infarction." Additionally, as exemplary concept "myocardial infarction" may be related in the taxonomy to concept "percutaneous coronary intervention" (as a "treatment" of myocardial infarction), a candidate instance/segment containing the text "percutaneous coronary intervention" may also result in a suggested concept of "myocardial infarction." Relationships between concepts in the taxonomy may be associated with relationship scores based on how closely the concepts are related, and this relationship score may be taken into account in estimating a confidence score. Methods associated with the data engine 106 may be used to execute this searching, and to assess, normalize, and adjust confidence, "hit", or similarity scores used to evaluate candidate instance-concept mappings. Each candidate instance may be associated with a score that denotes a confidence measure as to whether the candidate instance accurately maps to a concept. In certain embodiments, if a score is below a threshold, the candidate instance may be disregarded. In certain embodiments, entity instances are identified based on a subset of the segment types, such as sentences. In certain embodiments, a single entity instance may be evidenced in segments distributed across two or more documents associated with the same patient. In another example, documents may be scored with respect to one or more entities to assess the relevancy of the document to each of the one or more entities.

Instances in the input data may be linked to corresponding entities using various techniques, such as using annotations, tags, or a relational database, or may be extracted and associated with a patient. In one example, the entity may be represented in the document as one or more segments in the document, e.g., a particular sentence or three words in various locations in the document. This example instance may be associated with an identifier for the corresponding entity/concept, and that entity identifier may be associated with the document text using markup language tags around the particular sentence or three words in various locations in a marked-up enriched version of the document, where the markup tags further denote the entity identifier.

In step 506, additional entity extractors may be applied to the document. In certain embodiments, segments/candidate instances may be evaluated using additional separate taxonomies or dictionaries encompassed by data engine 106. These additional entity extractors may represent, for example, non-medical concepts or terms such as names (patients and other names), geographical terms, and molecules (such as drugs in development). An additional entity extractor may correspond to organization-specific terms associated with a set of patients. In certain embodiments, input documents may be annotated or tagged using one or more additional entity extractors. In certain embodiments, entities may be extracted from the documents and associated with one or more patients.

In step 508, rule-based annotators may be applied to the documents. These rule-based annotators may be used to augment and correct the entities and other annotations associated with each input document. Rule-based annotators may operate using, for example, section-specific annotators, semantic type annotators (including clinical guidelines—e.g., a machine-readable guideline 406), and base-term-type annotators. In certain embodiments, one or more rule-based annotators may be used to select proposed medical codes based on patient documents for a particular patient, or to propose a care plan for a patient. Rule-based annotators may additionally use subject-specific knowledge bases to provide information that the annotators may use in annotating the input documents with entities and other information. Step 508 is described more specifically with respect to FIG. 6.

In step 510, certain instances or terms in the document are evaluated to disambiguate word sense (e.g., where terms have homonyms). For example, a segment reciting "cold temperature" has a different meaning from "common cold." In certain embodiments, such word sense disambiguation proceeds by determining whether additional words suggest the correct context for an ambiguous term. For example, the procedure may analyze segments of one or more particular granularities that contain the ambiguous term to represent the context for the ambiguous term (e.g., other words in the same sentence, other words in the same paragraph, or other words in the same document). The procedure may analyze other words within 1, 2, 3, 4, 5, 10, 15, or 20, 50, or 100 words of the ambiguous term. In one example, the term "shingles" may appear within 50 words of the terms "disease," "herpes," or "acyclovir" in a document. In a different document, the term "shingles" may appear within 50 words of the terms "house" or "rain." Using, for example, a knowledgebase such as semantic taxonomy 206, terms in the context for the ambiguous term may be more closely associated with the disease sense based on the value or character of one or more concept attributes or concept relationships (e.g., because the disease "shingles" is caused by the virus "herpes zoster" and may be treated using the antiviral drug "acyclovir") than the building construction sense by scoring the relatedness between the document or segment and the concept "shingles (disease)" versus the concept "shingles (construction material)," or by using methods of step 504. In certain embodiments, data engine 106 may maintain a list or database of ambiguous terms and associated collections of diagnostic terms that indicate one or more particular contexts for the terms (e.g., for ambiguous term A, diagnostic term collections A1, A2, and A3, where each of A1, A2, and A3 are groups of terms associated with three different meanings, respectively, where the presence or absence of any term from A1, A2, or A3 may be used to disambiguate between the three competing meanings for ambiguous term A when term A occurs in a document or input data 101). In certain embodiments, the associated collections of diagnostic terms may provide positive and negative indications that an ambiguous term has a particular meaning and should be linked to a particular entity. In certain embodiments, individual diagnostic terms may be associated with weights so that terms more strongly associated or negatively correlated with a particular meaning for an ambiguous term may have a larger effect on the disambiguation decision than less predictive diagnostic terms. In certain embodiments, data engine 106 implements a method for correcting existing word sense errors in existing instance-entity mappings. In certain embodiments, data engine 106 implements a method for suggesting new instance-entity mappings based on ambiguous terms in segments. As a significant fraction of medical coding errors result from miscoding of a homonym, including word sense disambiguation methods avoids such errors and greatly improves the accuracy and usefulness of the resulting enriched data.

In step 512, coordinate expansion is applied to the input data 101, segments created in step 502, or candidate instances identified in step 504. Coordinate expansion refers to the steps of recognizing where two or more entity instances exist in a condensed grammatical form (e.g., by identifying multiple instances linked by conjunctions such as "and," "or", or punctuation such as '/'), and accounting for the existence of all the instances. For example, the text "Diabetes Type I and II" is expanded to recite two separate instances—"Diabetes Type I" and "Diabetes Type II." In another example, the text "lung/breast cancer" is expanded to identify "lung cancer" and "breast cancer." In certain embodiments, data engine 106 implements a method for correcting errors using coordinate expansion in existing instance-entity mappings (e.g., where a term such as "Diabetes Type I and II" is only identified as the entity "Diabetes Type I"). In certain embodiments, data engine 106 implements a method for suggesting new instance-entity mappings based coordinate expansion of text in segments. As a significant fraction of medical coding errors result from failure to recognize the existence of all instances where the are expressed in a condensed grammatical form, including coordinate expansion methods avoids such errors and greatly improves the accuracy and usefulness of the resulting enriched data.

In certain embodiments, process 500 may further include methods for automatically generating document summaries by aggregating linked entities/concepts and generating a textual summary based on attributes of those entities/concepts.

In certain embodiments, process 500 may further involve generating an index for each enriched document 108 or an index for each patient. Such an index may include references to linked instances/concepts or concept attributes, or an extracted list of entities/concepts. In certain embodiments, such an index may be used to quickly search enriched documents. The index and enriched documents may be formatted as, for example, an Apache Lucene™ search index, and the associated documents may be compatible with an Apache Cassandra™ data store, and an Apache Solr™ search server.

In certain embodiments, steps 504-512 may be performed in a different order than shown FIG. 5, or aspects of steps may be repeated. In certain embodiments, only a subset of steps may be performed. For example, medical abbreviations present in the input data 101 may be recognized as part of step 504, and institution-specific abbreviations and their mapping to entities/concepts may be handled in a subsequent step.

Figure 6:
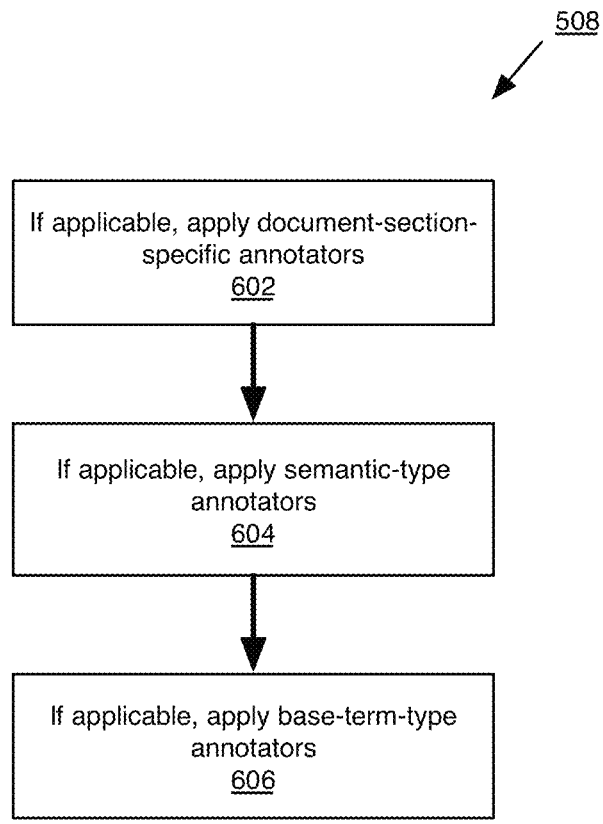
FIG. 6 shows a portion of a data enrichment process, consistent with some embodiments of the invention.

FIG. 6 shows an expanded description of step 508 of data enrichment process 500, in which rule-based annotators are applied to input data/documents. In certain embodiments, a clinical guideline may be used in a rule-based annotator. In certain embodiments, step 508 may involve three levels or categories of annotation that represent extracted entities, for example in which the annotators are applied as a stack in which higher level annotators can operate on the results or benefit from the processing of lower-level annotators in order to efficiently and more accurately annotate documents. In step 602, documents are annotated using higher-level section-specific annotators—for example, instances are identified and associated with entities (or corrected) based on information about where the underlying evidence occurred in a document. For example, a document may represent or include a medical history taken by a medical professional that documents a medical visit with a patient. The medical history document is likely to contain one or more of the following sections—chief complaint (e.g., a description of the health issue causing the patient to come in for the visit), history of the present illness, past medical history, family history, childhood diseases, social history (e.g., living arrangements, occupation, marital status, number of children, drug use (including alcohol, tobacco, and other recreational drug use), recent foreign travel, and the like), current medications (including prescribed and over-the-counter medications), allergies, and sexual history. In step 502, the document may have been broken into segments including sections. Using document-section specific annotators, candidate instances may be identified, or corrected because underlying evidence is located in a particular section of such a document. For example, if applicable, a chief complaint annotator, past medical history annotator, social history annotator, family history annotator, or pre- and/or post-surgery observations annotator may be used. In one example, a family history annotator may be used to avoid attributing to a patient a disease or condition supported only using evidence located in a family history section of a document, as it is likely that the diseases or conditions described in the family history section pertain to a relative rather than the patient. In certain embodiments, a document-section-specific annotator may initiate one or more semantic-type annotators and/or base-term-type annotators, and the annotations of the document-section-specific annotator may be dependent upon or rely upon the results or annotations of the semantic-type annotators and/or base-term-type annotators.

In step 604, semantic type annotators may be applied to segments. For example, a vital signs and observations annotator may be used to identify values for particular types of measurements based on patterns corresponding to measurement-value pairs, and accounting for common abbreviations—e.g., if a type of measurement such as "BMI" or "body mass index", or "heart rate" is found, the annotator may search for a trailing colon followed by a number. In certain embodiments, the annotator may further identify the units for the measurement, and may evaluate whether the number is within the range of possibility for a measurement of that type. (E.g., an extracted value of weight=2 might be discarded as an unrealistic value for common units such as kilograms or pounds.) In certain embodiments, an annotator may associate a type of observation with a qualitative value, such as "skin condition: flushed." A laboratory and test results annotator similarly may search in segments for the presence of test/value pairs (e.g., TSH (thyroid stimulating hormone), uric acid, or A1C/HbA1C (hemoglobin A1C, glycohemoglobin)) or panels of tests and result values (e.g., CMP (Comprehensive Metabolic Panel, including of 14 tests), hepatitis panel, or CBC (complete blood count)), where the values may be numerical or qualitative, such as "positive" where a tested condition is present. Additional semantic type annotators may include a drug and dosage annotator, a condition annotator, and a treatment procedures annotator, any of which may be based on a clinical guideline. In certain embodiments, semantic annotators may additionally use information about the context such as the section or type of document that includes the segment. In certain embodiments, annotators such as a condition annotator and treatment procedures annotator may apply one or more rules or clinical guidelines, such as machine-readable guideline 406a. In certain embodiments, a semantic-type annotator may initiate one or more base-term-type annotators, and the annotations of the semantic-type annotator may be dependent upon or rely upon the results or annotations of the base-term-type annotators.

In step 606, base-term-type annotators may be applied to segments. Base-term-type annotators may provide more specific information about an identified instance of a concept or other entity. Base-term-type annotators may include, for example, a negation annotator (e.g., determine if an instance or value is negated), an age group annotator (e.g., determine age of patient), a gender annotator (e.g., determine gender of patient), a geographic annotator, and a temporal value annotator. In certain embodiments, information from base-term-type annotators may provide the context to determine if, for example, a test result is within the normal range for the patient (e.g., where female and male patients are associated with different ranges, or expected values change based on age).

In certain embodiments, as part of any step of process 500, annotators may draw upon specific knowledgebases in order to identify additional entity instances and instance attribute values that are present in a segment or patient document. For example, specific knowledgebases may include code translations (to identify or tag, e.g., ICD-9 codes, CPT4, RxNorm), regular expression patterns (e.g., drug dosage patterns), temporal values, age values, geographic entities, semantic type concepts (e.g., Diseases, Laboratory tests, Drugs from semantic taxonomy 206), a database of document types and headings, a database of stemming, misspellings, and homonyms, clinical rules 210, and use-case-specific data, rules, and patterns.

In certain embodiments, steps 602-608 may be executed in a different order from the order shown in FIG. 6.

In certain embodiments, for a given entity/concept, patient documents may be ranked to identify the most relevant documents to the given concept using a ranking procedure. In one example, a concept search term may be associated with a concept for use in ranking documents responsive to the search term, e.g., by matching or finding the most similar value of a representative attribute of the concept compared with the search term, such as the concept with a matching/similar name or title (such that the concept search term is equivalent to the representative attribute of the concept). In certain embodiments, one or more attributes of an entity may be used as entity search terms for the entity. Ranking may be based on (1) the occurrences of an entity/concept in the document—that is, the count and/or location of instances of an entity within particular fields of the document (e.g., ranking based on finding the entity search term at one or more locations in the title and/or the body of the document) and (2) relationship strength—that is, the strength of the relationship between the given entity and the concept instances occurring in the document. For example, a relationship may be stronger if the given entity and a document concept instance are directly connected in a concept taxonomy (having an edge count or distance of "1" in a graphical taxonomy of concepts). A relationship may be weaker if the given entity and document concept instance are indirectly connected by intervening concepts in the concept taxonomy (having edge counts or distances between concepts of 2 or more). In certain embodiments, only positive relationships are included in determining concept distances of 1 or more.

In a more specific example, one or more occurrence scores may be calculated by assessing the number of instances of an entity (e.g., measured as the number of occurrences of an entity search term) in a field of a patient document, where the field may be the item title (e.g., in the file name or in the text title within a document), the section title, the keywords field, the MESH keywords field, the abstract, or the body of the document. In certain embodiments, a higher score corresponds to a higher number of occurrences, and indicates greater relevancy to the given entity search term. For one or more fields, such as the body, the number of occurrences may be weighted according to where the instances are located within the field (e.g., higher weight earlier in the value for the field, and lower weight toward the end of the value or text).

Occurrence scores may be weighted by multiplying or adding a boost value to obtain a base score for one or more of the fields. Occurrence scores associated with the given entity for the patient document may be used to rank patient documents. A boost value is a positive or negative weighting factor. The boost values may be specific to particular fields. Base scores may thus be based on a combination of weighted occurrence scores. Base scores may be limited to a maximum base score by a threshold or cut off value. Base scores associated with the concept may be used to rank patient documents with respect to the given entity.

A relationship score for the patient document and given concept may be based on the base scores for instances of concepts/entities in the document that are related to the given entity, for example where a higher score indicates a stronger relationship. In certain embodiments, these related concepts must have a positive relationship to the given concept. For example, a positive relationship indicates that the two concepts have some positive semantic correlation, whereas in certain embodiments a negative relationship indicates that the two concepts are negatively correlated—i.e., the presence of one concept means that the second concept is less likely to be true or present. In certain embodiments, certain entities/concepts that might otherwise be related to the given entity are filtered out and not included in a relationship score, for example based on the value of an attribute or membership in a group. The relationship score may be the sum or product of the base score of related concepts (as indicated to be related by a graphical taxonomy structure) where the related concepts have an edge distance of 1, 2, or fewer than 3 edges relating the given entity to a related document concept. The relationship score may be the sum or product of a set of scores assessing the strength of the relevance of an individual document instance of a concept/entity to the given entity, where each of the set of scores is associated with an instance that is connected to the given concept in a taxonomy. In certain embodiments, relevance of an individual document instance of a concept/entity to the given entity may be based on, for example, a count of the number of instances of a query term/given entity in the document. The relationship score may be limited to a maximum value by a cutoff value, and/or re-scaled by a scaling value.

A title score may be calculated based on a count of the number of instances/occurrences of a query term/given entity in the title of the document. For purposes of the title score, the title of the document may be one or more of the file name, the title or headline appearing within the document, and section titles appearing within the document. The title score may be affected by the location of the query term/given entity within the title (i.e., where appearing earlier in the title leads to a higher score indicating greater relevancy), and the length or number of words in the title (i.e., where a greater length or larger number of words reduces the title score).

A map relevancy score may be calculated based on a combination of an occurrence score or base score, a relationship score, and a title score. Such a score may be adjusted or normalized based on the body length—for example, the score may be scaled inversely with the length of the body of the document.

In certain embodiments, documents in a set of documents or database may be ranked with respect to a query term or given entity based on one or more of an occurrence score or base score for the term/given entity, relationship score for the term/given entity, title score for the term/given entity, and/or map relevancy score for the term/given entity—for example, if a high score indicates better relevancy or a better match, the documents scoring higher than a threshold or the top 1, 2, 5, or 10 documents may be provided in response to a request for the top-ranked documents for a search term. In certain embodiments, a lower score may indicate a better match or better relevancy, and the documents scoring below a threshold may be provided in response to a request for the top-ranked documents for a search term.

In certain embodiments, occurrence scores, base scores, relationship scores, title scores, and/or map relevancy scores may be pre-calculated for a set of query terms or entities and stored in an index for a quick look-up. In certain embodiments, one or more of these scores may be calculated on an as-needed basis, for example at the time that a search term is provided by a user via a search user interface as a query term.

One specific example method for scoring documents is as follows:

(1) count the number of occurrences of concept in title, keywords, and other fields except body. Oti=the number of occurrences of concept in item title; Ots=the number of occurrences of concept in section title; Ok=the number of occurrences of concept in keywords; Okm=the number of occurrences of concept in mesh keywords; Oa=the number of occurrences of concept in abstract.

(2) calculate the body base score. Ob=the sum of (1−position/body length).

(3) calculate the base score for title, keywords, and body with boost value. Bt=boost value for title (default 8); Bk=boost value for keywords (default 4); Bb=boost value for body (default 1); B'=(Oti*Bt+Ots*Bt)+(Ok*Bk+Okm*Bk+Oa*Bk)+Ob*Bb.

(4) adjust the large base score for body and keywords. Cb=cutoff value linear to logarithmic (default 32); B=B' (B'<=Cb); B=Cb*(1+log(B')−log(Cb)) if (B'>=Cb).

(5) remove concepts if part of an exceptions group.

(6) calculate a positive relationship score. P'=the sum of base score of positive concepts which has relationship with the concept with distance 1.

(7) adjust large relationship scores. Cp=cutoff value linear to logarithmic (default 48); P=P' if (P'<=Cp); P=P'+(log (Cp))**2/(log(Cp)−1)*(P'/log(P')−Cp/log(Cp)) if (P'>=Cp).

(8) adjust the relationship score. P=P*0.5.

(9) calculate the title special score (for itemtitle and sectiontitle). Br=term word count ratio boost value (default 64); Bp=term position boost value (default 32); Wc=the number of words of term (concept); Wt=the number of words of title; Pc=the position of term (concept) (in char); Lt=the length of title (in char); T(i|s)=(Wc/Wt)^2*Br+(1−(Pc/Lt)*Bp; T=Ti+Ts.

(10) calculate map relevancy value as reference. M'=B+P+T.

(11) adjust map relevancy value with body length. Wb=the number of words of body; M=0 if (Wb<=50); M=M'*(Wb−50)/100 if (50<=Wb<=100); M=M'*(0.5+(Wb−100)/800) if (100<=Wb<=500); M=M' if (500<=Wb<=1500); M=M'*(1−(Wb−1500)/2500) if (1500<=Wb<=2000); M=M'*0.8 if (Wb>=2000).

(12) adjust map relevancy value for Anatomy STY group. M=M*0.25 (if Anatomy STY group); M=M (otherwise).

(13) store M, B, P, T and Ob separately in the concept index and report them.

Figure 7:
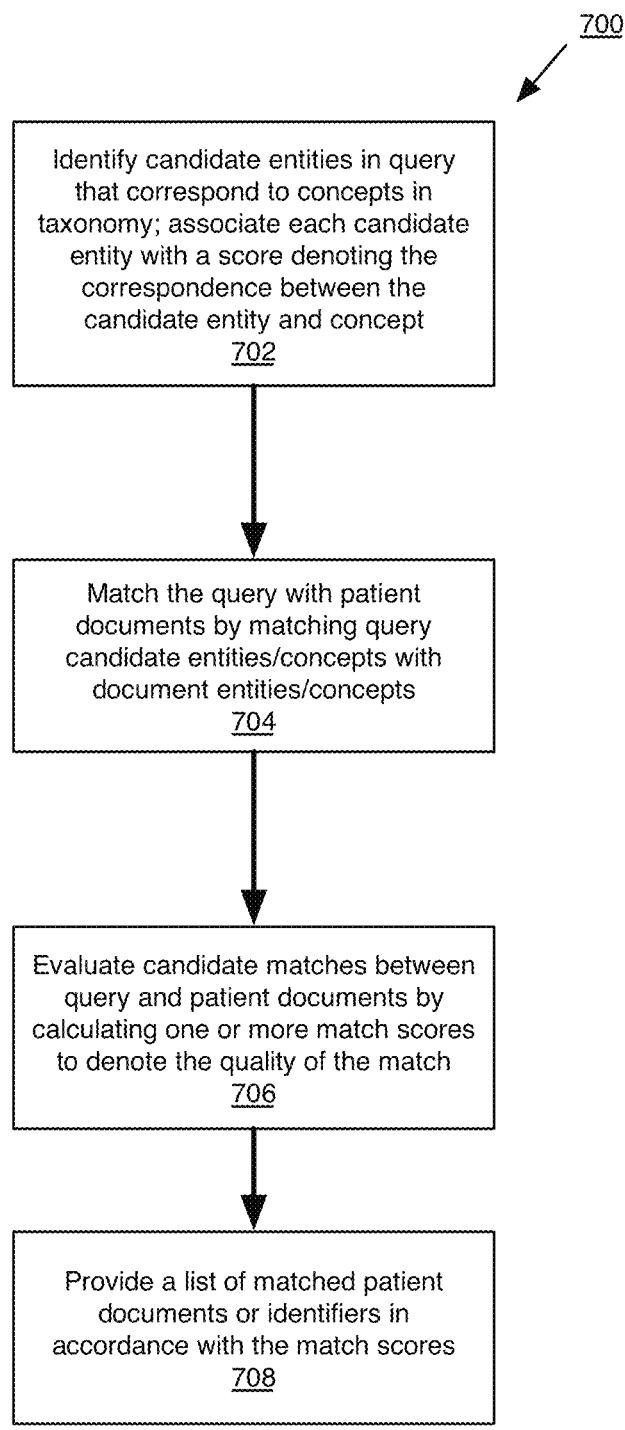
FIG. 7 shows a process for searching using a data engine, consistent with some embodiments of the invention.

FIG. 7 shows an exemplary process 700 for searching enriched patient documents 108 using a data engine to identify enriched documents that are relevant to the query. In certain embodiments, documents may be searched using a natural language text query. In certain embodiments, a structured query, or keywords may be used for searching.

In step 702, a query is processed to identify concept instances in the query text that correspond to concepts in semantic taxonomy 206. In certain embodiments, this identification of instances in the query text uses the same or similar methods to those described in step 504 of method 500. In certain embodiments, the enriched documents will be searched using query entities/concepts that correspond to instances that exceeded a threshold score.

In step 704, data engine 106 will identify enriched documents that are also associated with the query entities/concepts, e.g. by searching an index for each enriched document 108 with each query entity. In certain embodiments, semantic taxonomy 206 will be used to identify concepts that are related to the query entities via concept relationships 306, and the resulting universe of entities/concepts will be used to search the enriched documents 108 and identify matching documents/patients.

In step 706, the matches between the query entities and patient documents will be evaluated by calculating one or more match scores to denote the quality of the match. Such a score may be based on an evaluation of the strength of the relatedness of query and hit entities/concepts in semantic taxonomy 206, or another measure of similarity. Matches below a threshold score may be discarded. In certain embodiments, the identification of enriched documents that may be relevant to the query entities (step 704) (that is, matches or hits to the query entities) and scoring of matches (706) may be performed by searching an index of enriched documents, where each document is associated with scores for ranking each respective document in accordance with the document's relevance to one or more concepts or search terms. In certain embodiments, identification of matches to the query entities may be performed by evaluating whether the search terms are implicated in the documents on demand, in response to receiving the query (e.g., each of a set of documents will be evaluated as to whether they contain instances of the query entity by annotating or enriching the documents with respect to the query entity).

In step 708, a list of matched patient documents, or identifiers to the matched documents may be provided. In certain embodiments, a list of patients (e.g., patients associated with the matched patient documents), or a list of objects generated based on entities instantiated in the documents may be provided (e.g., information extracted from the matched documents and provided in a different form). In certain embodiments, the list of documents may be organized by patient, and/or by the strength of the match score.

In certain embodiments, the query may be converted to a test that patients associated with enriched documents must meet—for example, patients who are undiagnosed but may have chronic kidney disease based on out-of-range readings for eGFR and microalbumin tests, or patients satisfy clinical guidelines for Type II diabetes.

Figure 8:
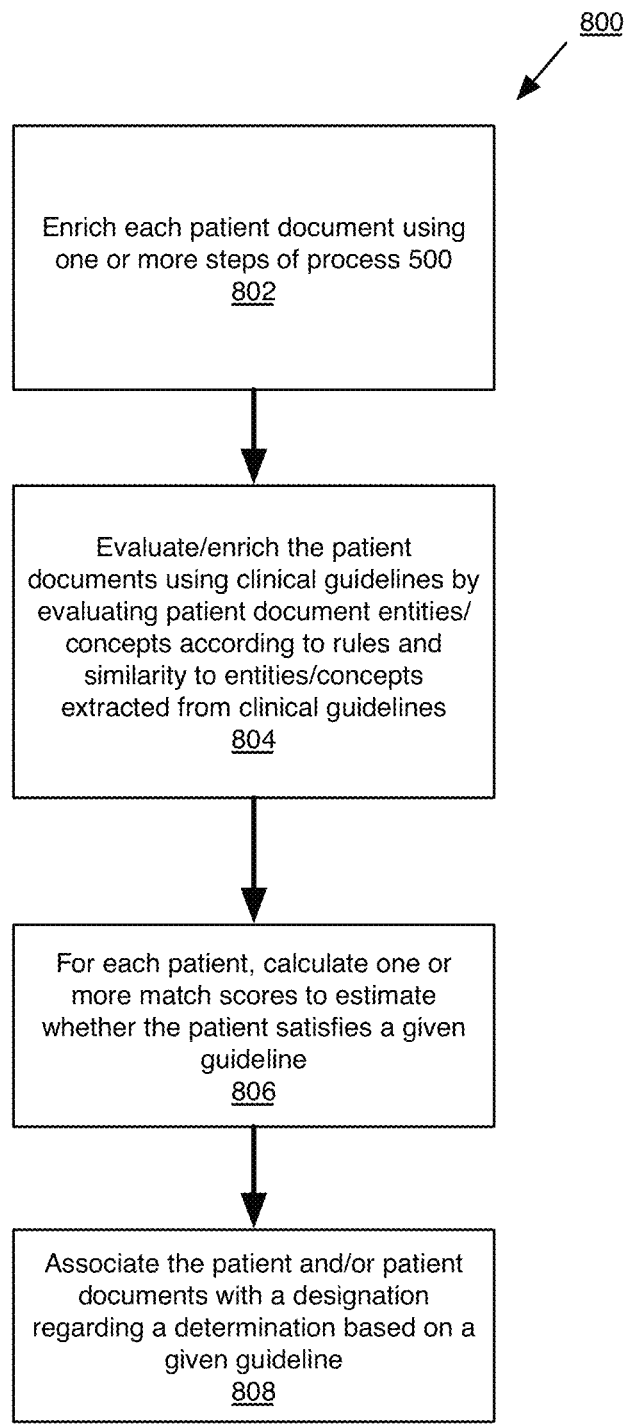
FIG. 8 shows a data enrichment process concerning clinical guidelines, consistent with some embodiments of the invention.

FIG. 8 shows an exemplary data enrichment process 800 concerning clinical guidelines. A user may wish to identify all patients in a population that satisfy a particular clinical guideline: for example, patients who satisfy clinical guidelines for Type II diabetes. The user may have certain patient documents related to that patient population—e.g., longitudinal patient data from electronic medical health records for the patient population. The clinical guideline of interest may be imported into data engine 106 and clinical rules 210 using, for example, the methods described in connection with step 208 of process 200 and FIG. 4.

In step 802, the patient documents may be enriched to identify entities including clinical measurements and their values using, for example, one or more steps of process 500.

In step 804, the patient documents may be evaluated using the clinical guidelines of interest by evaluating the patient document entities/concepts and attributes according to the rules extracted from the clinical guidelines, and for example enriching the patient documents, descriptions of particular patients, or patient records, using the results of one or more constituent rules and the overall guideline. See also the discussion of evaluating clinical rules in connection with FIG. 4.

In step 806, for each patient, a match score may be calculated to estimate whether the patient satisfies the clinical guideline. In certain embodiments, an evaluation of the confidence in the result of any individual clinical rule or overall clinical guideline (e.g., a statistical evaluation of the quality of the evidence or the inference based on the guideline) may be associated with the patient or a patient document.

In step 808, the patient and/or patient documents may be associated with a designation, such as a concept or attribute regarding a determination based on a given guideline. Process 800 may alternatively provide one or more lists of patients falling into various categories with respect to the clinical guideline (e.g., list of patients meeting clinical guideline and list of patient not meeting clinical guideline, or have a particular classification under the guideline).

In certain embodiments, data engine 106 may be configured to generate and compare cohorts of patients having a particular annotation or set of annotations. For example, process 800 may be used to identify one or more cohorts of patients having a particular condition as defined by a clinical guideline.

For example, a clinical guideline (or similar set of rules) may be used to identify a group of patients who are likely to have a condition but have not been diagnosed with the condition. Data engine 106 may be used to identify all patients within a population who have not been diagnosed with chronic kidney disease by analyzing claims documents for the population, and excluding patients who are associated with a claim for treatment of chronic kidney disease (using, for example, process 500 to enrich the claims documents and identify patients already treated for or diagnosed with chronic kidney disease). Next, laboratory data for the patient population may be analyzed using two clinical rules associated with diagnosing chronic kidney disease: rules defining out-of-range readings for eGFR and microalbumin tests, using, for example, process 800. Data engine 106 may be configured to execute each of these processes, and to compare the second group patients associated with out-of-range readings to the first group of patients who have already been diagnosed with chronic kidney disease, and return the patients in the second group who are not also in the first group. Such a technique may be used to identify individuals with untreated or undiagnosed health issues who might benefit from proactive efforts to notify the patient or patient's practitioner and potentially provide additional care to the patients, rather than allowing care to be delayed until the next hospital or doctor visit.

In another example, a set of rules executing via data engine 106 may be used to propose optimal post-hospital discharge care for a patient. Certain socioeconomic factors are predictive of whether a patient may be shortly readmitted to a hospital after receiving care at a hospital. Frequently, a subsequent readmission suggests that the patient did not receive adequate post-discharge health services. Accordingly, a proposed post-discharge care plan designed to minimize inadequate post-discharge services may be based on socioeconomic data, such as a credit history or credit score from a credit bureau such as Equifax, TransUnion, or Experian, and non-medical factors such as whether the patient lives alone, the geographic location of the patient's residence, and the patient's income. Data engine 106 may propose a care plan by (1) identifying one or more needed post-acute-care health services based on the patient's health conditions (as evident from documents and other records of the patient's healthcare, e.g., using concept relationships in semantic taxonomy 206), and (2) proposing post-acute care resources capable of handling the needed post-acute-care health services based on the patient's socioeconomic or psychosocial data (e.g., proposing geographically appropriate post-acute care resources such as home health aids or care givers, medical malpractice attorneys), including contact information and names of providers. In certain embodiments, such proposed post-acute care resources may be assigned a score and prioritized using factors including, for example, estimated cost, coverage by the patient's health plan, and geographical distance from the patient's residence.

In certain embodiments, the knowledge bases and rules used by step 508 of process 500 may include a set of rules configured for selecting proposed medical codes based on patient documents for a particular patient, using data engine 106. Medical codes may be used to document health services for a patient, and to estimate the risk level of a patient and a population of patients. Automated generation of proposed codes using data engine 106 to mine structured and unstructured patient data enables coding of patient conditions that would otherwise be missed using a manual coding process. Proposed codes may be represented as attributes or instances of entities in enriched data 108. Proposed codes may be based on (1) evidence supporting a particular diagnosis that is present in the enriched patient documents using, for example, the processes described above (e.g., process 500 and 800), (2) whether a code has already been associated with the patient during the current health plan year (e.g., based on a rule that if a condition continues to exist in the patient, it may be claimed once per health plan year), and (3) given multiple applicable codes, which code most accurately describes the patient's condition.

Certain embodiments of the user interfaces described herein facilitate a user's ability to review and generate documentation for medical codes found in a patient's medical record. Certain embodiments of the user interfaces described herein facilitate a user's ability to review and generate documentation for healthcare quality measures and care gaps found in a patient's medical record. Certain embodiments of the user interfaces described herein facilitate a user's ability to review and generate documentation for clinical (e.g., conditions, treatments) and non-clinical (e.g., patient ID, addresses, provider names, dates of service) entities that may be captured from a patient's chart. Certain embodiments of the user interfaces described herein facilitate a user's ability to review and generate documentation for clinical decision support prompts, for example identifying medical conditions, medications, treatments, care gaps, and other clinical information that is surfaced (e.g., as identified entities) along with associated evidence, that can support a clinician's ability to make a more informed clinical judgment regarding the patient's care plan. These features may improve the outcomes of a patient's care plan, and help with more efficient use of health care resources.

FIG. 9 shows an exemplary user interface 900 for documenting missing diagnosis codes for a single patient. User interface 900 includes two main panels: panel 902 presented on the left of user interface 900, which is shown to display a third of six patient documents (see document selector 903), and panel 904, which shows aspects of a series of proposed code sub-panels 906. In panel 904, the proposed codes are ordered by risk adjustment factor (RAF) adjustment. A risk adjustment factor is an assessment of the health risk associated with a patient under a particular risk model, for example the Centers for Medicare and Medicaid Services (CMS) Hierarchical Condition Category (HCC) model. A risk adjustment factor may be based on patient health status and demographic characteristics. A RAF adjustment is the amount by which a patient's RAF will change—for example, the amount the RAF will change if a proposed code is accepted in user interface 900, thus adding another health issue to the evaluation of the patient's health status. Proposed codes shown in panel 904 may additionally or alternatively be ordered by evidence position within the patient documents, RAF adjustment, proposed code number/name, or document type. In FIG. 9, by accepting the proposed code in sub-panel 906*a*, the RAF adjustment is 0.691, meaning that if the proposed code is accepted, the RAF for the patient will increase by 0.691. Accordingly, by ordering the proposed codes in order by RAF adjustment, a user may consider the proposed codes prioritized by the magnitude of their impact on the patient's RAF. This can assist the user in identifying health issues that might otherwise be overlooked, resulting in a more accurate and comprehensive assessment of the patient's health status as incorporated into the risk adjustment factor model. RAF adjustments for the patient population can be continuously updated as coding of the documents proceeds. User interface 900 is intended to facilitate review of all documents associated with a patient, one document at a time, to review existing codes, correct miscoded conditions/services, and assign new codes to document un-coded medical services or conditions in a patient that are evidenced by each document.

The proposed code in sub-panel 906*a* corresponds to an ICD-10 code for Parkinson's Disease, G20. The evidence for the proposed code in sub-panel 906*a* is shown in panel 902, which displays a "Patient Plan" document for the patient (i.e., the third of six documents as indicated by document selector 903). The Patient Plan document is scrolled to the location of the strongest or most important evidence underlying the proposed code in sub-panel 906*a* and identified using an evidence tag 908*a*—in this example, the evidence is a notation of "Parkinson's Disease (332.0)" in the Patient Plan. In certain embodiments, the most important evidence is the evidence most strongly suggesting a proposed code, or the evidence making the largest contribution to RAF. In certain embodiments, the evidence tag is displayed as highlighting, underlining, bolding, other emphasis, or using an overlaid icon. For example, evidence used to support a proposed code under a particular model may be identified using a particular type of emphasis, such as highlighting in a particular color corresponding to the model (e.g., yellow highlighting of evidence corresponding to proposed codes based on the HCC model). In certain embodiments, the user may cycle through one or more evidence tags 908 (e.g., 908*a* and 908*b*) to view each item of evidence underlying a proposed code/concept using a link, button, or other user interface control, and with each new current evidence tag, the relevant document in panel 902 is scrolled to the location of the current evidence tag. Document selector 903 may indicate both which numbered document is being displayed in panel 902 and which documents include evidence that has been identified to support the current proposed code (see, e.g., an indicator—here, a horizontal bar—positioned over the numbered document containing evidence supporting the code); a second type of emphasis in document selector 903 indicates the currently displayed document (e.g. highlighting of the current document number).

Each sub-panel 906 may include action controls for marking a preliminary or final status as part of a work flow: e.g., the option to accept (i.e., confirm the proposed code), reject the code, or mark the code for further review. Sub-panel 906*a* shows a "comments" drop-down control that allows the user to tag a proposed code with comments such as "Does not meet the M.E.A.T. Criteria"; "Not an active condition/Historical"; "Incorrect inference/not supported"; "Already billed for the current plan year"; or "other." Sub-panel 906*a* may additionally permit entry of free-text comments to be associated with the code.

The sub-panels 906 further include user interface controls for cycling through a sequence of proposed codes (see up/down arrows in subpanel 906*a*), and panel 904 includes an additional user interface element 910 (e.g., the vertical line with selectable dots corresponding to different sub-panels 906) for cycling through a sequence of proposed codes. The user interface may further support keyboard commands for moving to the next or previous code. Panel 904 shows selectable peeks 912 of additional proposed code subpanels 906; upon selection, peeks 912 expand to present a corresponding sub-panel 906.

In certain embodiments, a panel 902 may be used to present various types of patient documents, for example, a patient's chart. Panel 904 may be used to present sub-panels 906 (and selectable peeks 912, e.g. peek 912*a* and peek 912*b*), such that each sub-panel 906/peek 912 presents a suspected disease or condition. Predictions resulting in suspected diseases or conditions may be based on the content of the patient's chart, based on one, two, three, or more predictive models. The evidence supporting a particular suspected disease may be highlighted in the patient's chart (shown in panel 902) in a manner that corresponds to the model on which the prediction is based. (E.g., for a suspected disease X, presented in a sub-panel 906, with a prediction based on an HCC model, all supporting evidence in the chart may be highlighted with a color associated with the HCC model, such as yellow or red highlighting.) In certain embodiments, the highlighting may indicate a distinction between evidence highlighted as supporting the in-focus or current proposed code/disease in a panel 906 as distinguished from evidence that is color coded under the same prediction model but supporting a different proposed code/disease—for example, highlighting border vs. no border, stronger or more opaque highlighting vs. faded or less opaque highlighting. The sub-panel 906 may present, e.g., a code, textual label, and description of the suspected condition, as well as information such as the date of service, rendering provider, page number within the chart, an input box for receiving comments, and a display for any additional evidence that has been attached to the suspected condition (e.g., following a sequence similar to the use of window 1102 and additional evidence 1202 as explained below). In certain embodiments, separate controls may be respectively provided for scrolling through or displaying, in sequence, (1) highlighted evidence in patient documents, (2) patient documents (e.g., 903), and (3) proposed codes/predicted conditions/identified concepts (e.g., up/down arrows in sub-panel 906; element 910).

In certain embodiments, user interface 900 will clearly show the patient's name and supporting healthcare information (e.g., date of birth, gender, primary provider, patient ID). In certain embodiments, it will further provide workflow elements for optimizing processing of patient data (e.g., interactive checkboxes for marking coding as complete, and for marking quality assurance (QA) as complete (and in some examples, text boxes or other user interface controls for receiving QA-related comments), for example to track progress with processing a set of patient records). In certain embodiments, QA user interface controls are only displayed after an encounter is marked as "coding completed" (where an "encounter" is, e.g., a grouping associated with patient document or set of documents related to a patient care event)

In certain embodiments, the user interface will provide a user control for accessing/viewing an original version of the document shown in panel 902 (e.g., a scanned PDF or raw text). In certain embodiments, the patient document in panel 902 and the current sub-panel 906 are synchronized—that is, as the user cycles through the sequence of proposed codes/suspected diseases, sub-panel 906 presents the current proposed code or suspected disease, and the chart or document presented in panel 902 is scrolled to the first or most important supporting evidence for the current code/disease. The most important supporting evidence may be the information providing the largest contribution to a score associated with the associated prediction model (e.g., HCC, RxHCC, and the like).

In certain embodiments, user interface 900 may be compatible with protected health information (PHI) best practices—for example, any display of the original document in panel 902 or a pop-up window may automatically close, and the information in panel 902 may refresh if the user selects a different patient in the user interface. This may avoid patient mismatch issues where a window or panel shows one patient's information while another area of the user interface shows data for another patient. In certain embodiments, a particular patient's data may be locked so that it cannot be altered via user interface 900 until the patient is unlocked via a special interface, for example by a user of the system having specified super user or administrator privileges.

In certain embodiments, user interface 900 may include a panel displaying already coded concepts—e.g., a listing of accepted codes for a patient or for a particular period of time for the patient. In certain embodiments, user interface 900 provides controls for accessing the next or previous patient information from a list of patients. In certain embodiments, the ordering of such a list of patients is based on the ordering of patients in a different user interface, such as user interface 1700 described below.

FIG. 10 shows another view of exemplary user interface 900 for documenting health services for a patient, showing an aspect of associating additional evidence with a proposed code. User interface 900 may be used to create new codes to be associated with the patient, as well as to tag a proposed code with additional evidence in the patient documents. Panel 904 displays a second proposed code in sub-panel 906b, concerning an absence of a great toe. Document selector 903 indicates that the first of six documents is displayed in panel 902 using a first type of emphasis. Document selector 903 additionally indicates that evidence supporting the currently displayed proposed code in sub-panel 906b is located in the second document using a second type of emphasis (e.g., using a bar displayed over the link to document 2). A user may notice that the first document, a "nurse master", includes additional support for the "Z89.412: Acquired absence of unspecified great toe" code shown in sub-panel 906b. Shown in panel 902 under the heading "Chronic conditions" in the first document is a notation of "Left Great Toe Amputation."

Figure 11:
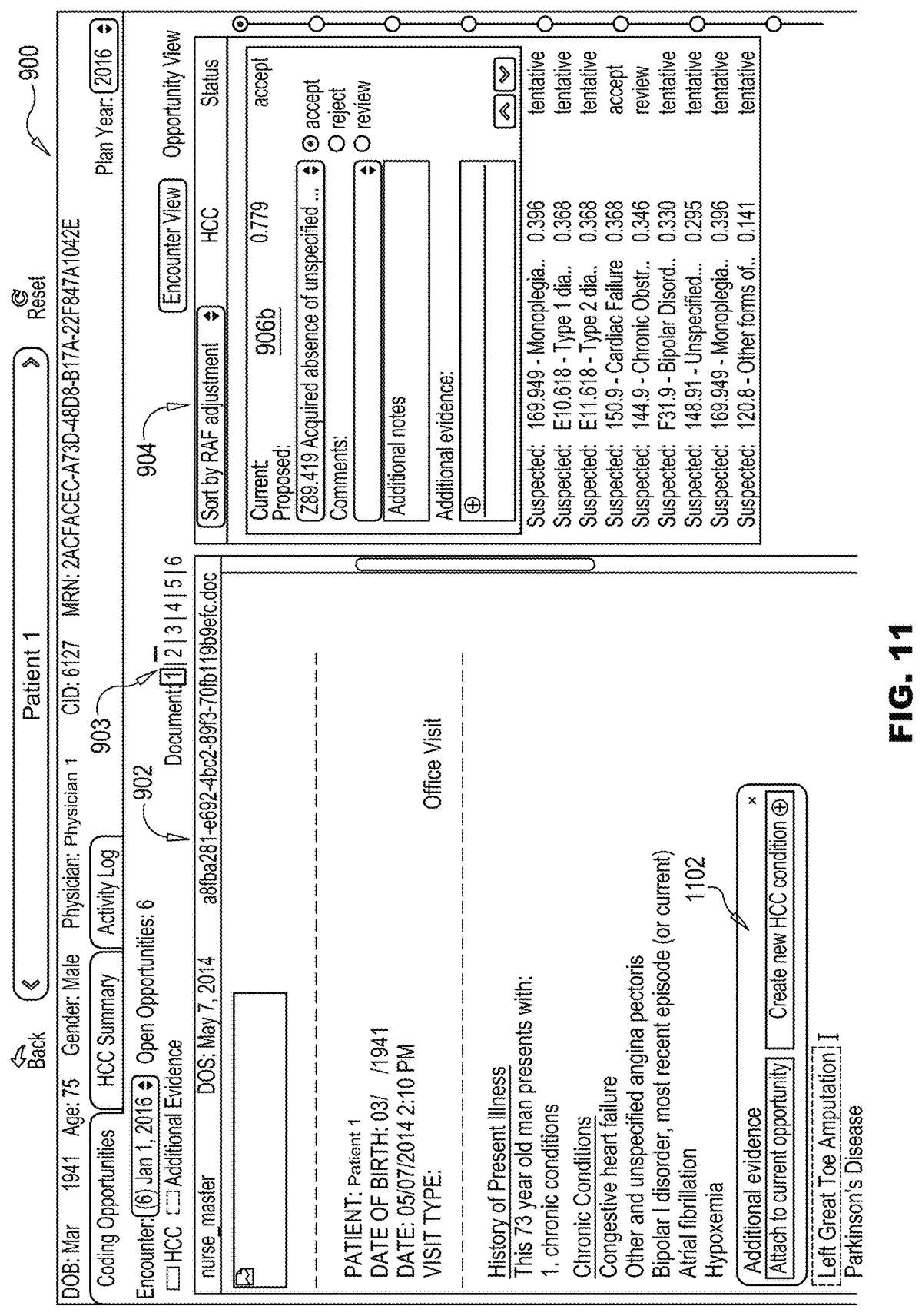

FIG. 11 shows another view of exemplary user interface 900 for documenting health services for a patient, showing another aspect of associating additional evidence with a proposed code. A user has selected the text "Left Great Toe Amputation" in the document shown in panel 902 by highlighting the text in the displayed document, causing an "additional evidence" window 1102 to appear. In this example, the highlighting is a different type of emphasis from the differently-appearing highlighting of evidence underlying proposed codes following the HCC model. Window 1102 provides selectable user interface elements for attaching the selected text to the current opportunity (i.e., the current proposed code in sub-panel 906b), or to create a new code supported by the selected text as evidence (e.g., create a new HCC condition as an example of defining a new concept). In certain embodiments, user interface 900 may include a user interface control for adding a new concept/entity to an associated data store or knowledgebase (e.g., via window 1102, or positioned within panel 904). Upon selecting the control, the user may define the new concept by adding attributes such as a name and a description, and may then indicate that the current document in panel 902 provides evidence of the presence of the new concept.

FIG. 12 shows another view of exemplary user interface 900 for documenting health services for a patient, showing another aspect of associating additional evidence with a proposed code. After the user selects the option to attach the selected material to the current proposed code in window 1102, the selected evidence appears in sub-panel 906b as additional evidence 1202, and the associated material in the first document is emphasized using evidence tag 908b in panel 902. In certain embodiments, evidence tags may have a different appearance based on the type of evidence they are associated with—for example, evidence proposed under a particular risk model may be highlighted in one color, and evidence marked as additional or supporting evidence may be highlighted in a second color.

Figure 13:
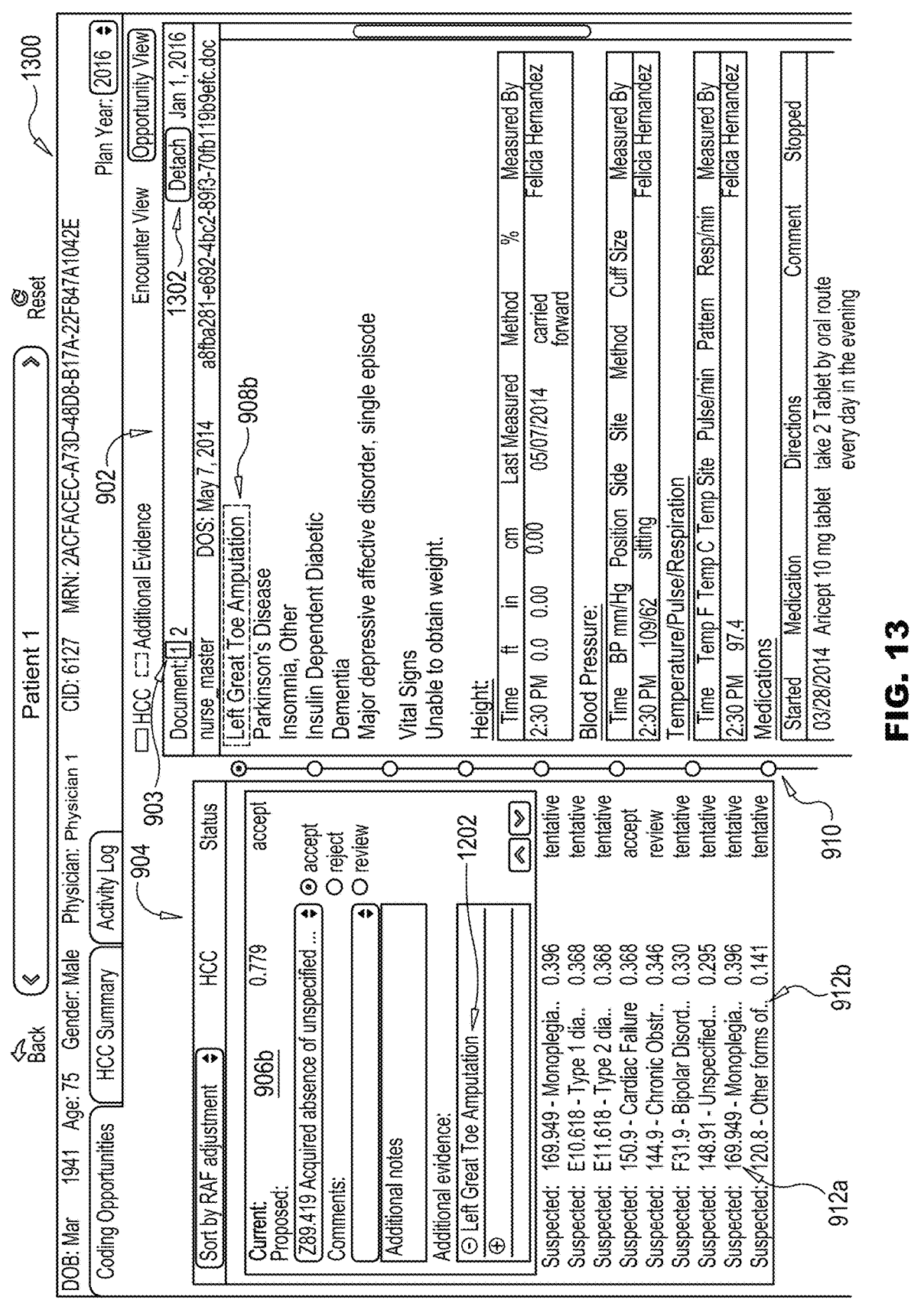

FIG. 13 shows a different exemplary user interface 1300 for documenting health services for a patient ("Opportunity View", as contrasted with "Encounter View"). User interface 1300 shows proposed codes in a panel 904 on the left, and one or more documents that are relevant to the current proposed code in a panel 902 on the right. In user interface 1300, only the documents containing evidence relevant to the code displayed in the current sub-panel 906 are available for display in panel 904. Document selector 903 shows that the first of two documents containing evidence associated with the code in sub-panel 906b is currently displayed in panel 904. (E.g., in the example provided here, document 1 is the document containing additional evidence 1202 of code Z89.419, and document 2 is the document containing evidence under an HCC model to support proposed code Z89.419; documents 3-6 are not shown via document selector 903 as they were in user interface 900, providing an example of an Encounter View.) User interface 1300 is intended to facilitate review of each medical code associated with a patient, one code at a time, to review, correct, and assign additional evidence to support medical codes to document medical services or conditions in a patient. Selectable user interface element 1302 allows a document to be detached from a code or a patient. In certain embodiments, where multiple documents or charts contain evidence supporting the recommended condition or proposed code, the user interface may provide a split-screen display (e.g., showing each evidence document appropriately highlighted (e.g., color coded to match the prediction model) and auto-scrolled to the location of the supporting evidence (see, e.g., FIG. 20). Such a user interface may divide panel 902 into multiple panels, each panel presenting a different document or patient information, e.g. from different sources, represented as different documents. In certain embodiments, a user interface control is provided to zoom in or zoom out on the document displayed in panel 902.

FIG. 14 shows another view of exemplary user interface 1300 for documenting health services for a patient. Document selector 903 shows the second of two documents, a "lab requisition" document, containing evidence associated with the code in sub-panel 906b is currently displayed in panel 904. In certain embodiments, portions of two or more documents may be displayed in panel 904 at one time, scrolled to show the portion of each document that contains evidence associated with the currently displayed code in panel 902.

Figure 20:
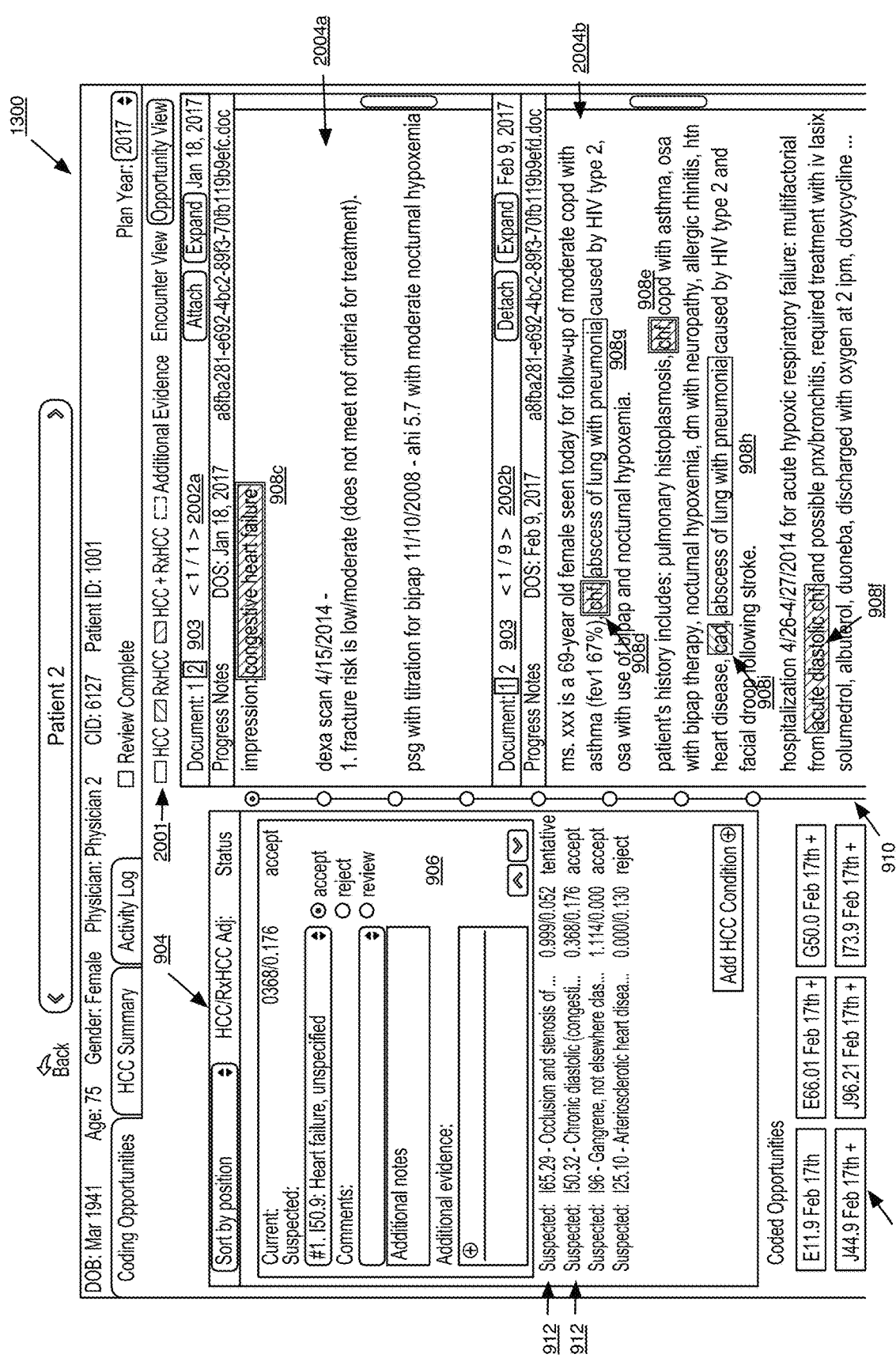
FIG. 20 shows an exemplary user interface concerning documenting health services, consistent with some embodiments of the invention.

FIG. 20 shows another embodiment of exemplary user interface 1300 for documenting health services for a patient. This user interface may be appropriate for showing a user how one or more proposed codes is supported by evidence in more than one document, by identifying and displaying the particular evidence (e.g., information such as textual terms) in the documents that the proposed code is based on in a manner so that a user can review the context of the evidence. In this embodiment, panel 902 simultaneously displays portions of two different patient documents in document sub-panels 2004a and 2004b (e.g., Progress notes from date of service Jan. 18, 2017 in sub-panel 2004a, and Progress notes from date of service Feb. 9, 2017 in sub-panel 2004b). A portion of each sub-panel 2004 presents a document selector 903; in this example, the second of two documents is displayed in subpanel 2004a (as shown by emphasis in the respective document selector 903) and the first of two documents is shown in sub-panel 2004b. A portion of each sub-panel 2004 additionally presents an evidence selector 2002, for navigating through evidence that is highlighted or emphasized in the respective document and that corresponds to the proposed code in current sub-panel 906 in panel 904. In the example shown in FIG. 20, evidence selector 2002b indicates that a total of nine evidence tags 908 found in document 1 (shown in document sub-panel 2004b) support the current proposed code ("I50.0: Heart failure, unspecified), and evidence selector 2002b may be used to move forward and backward through that sequence of nine evidence tags 908 (e.g., by selecting a forward target ">" or a backward target "<"). In certain embodiments, upon display of a proposed code in sub-panel 906, the related documents are automatically scrolled to the first supporting evidence tag in those documents.

In the embodiment of user interface 1300 shown in FIG. 20, a portion of panel 902 presents evidence category legend 2001 (e.g., indicating categories of "HCC," "RxHCC," "HCC+RxHCC," and "Additional evidence." Evidence tags 908 shown in the documents presented in panel 902 may be highlighted according to their evidence category as indicated in the legend—e.g., to indicate the model on which the predicted evidence is based. Additionally, evidence corresponding to the current proposed code shown in the current sub-panel 906 in panel 904 may be presented as in-focus using additional emphasis, such as a special border or variation on the highlighting color that may be indicated by the evidence category legend 2001. In certain embodiments, evidence tags that are not in-focus are presented as faded and without a special border. Evidence selector 2002 may be used to cycle through each in-focus evidence tag 908 in the corresponding document. For example, upon selecting the forward or backward indicator in selector 2002, the corresponding document may be scrolled to display the next or previous in-focus evidence tag 908, where the tags are ordered by, for example, importance to the proposed code or by their location in the document. Upon selecting a different proposed or suspected code via user interface element 910 or a peek 912, panel 904 will present a new current sub-panel 906 showing the newly selected proposed code, and each evidence selector 2002 may automatically indicate the appropriate number of evidence items supporting the new proposed code in each document (e.g., if a particular document does not contain any supporting evidence tags for the new proposed code, the corresponding evidence selector 2002 may indicate 0/0, or in some embodiments, the document may be removed from the display).

In certain embodiments, evidence tags 908 are presented as in-focus when they are used to support the current proposed code shown in sub-panel 906. In certain embodiments, evidence tags 908 are presented as in-focus when they represent the current tag 908 as selected using an evidence selector 2002. As shown in FIG. 20, exemplary evidence tags 908c-e are in-focus and represented as belonging to the "HCC and RxHCC" evidence category, and in-focus evidence tags correspond to the current proposed code. Evidence tag 908f also belongs to the "HCC and RxHCC" evidence category but is not in-focus. Evidence tags 908g and 908h belong to the HCC category and are not in-focus, and tag 908i belongs to the RxHCC category and is not in-focus.

FIG. 20 additionally presents a collection of coded opportunity notes 2010. Coded opportunity notes 2010 may be used to indicate a previously finalized code and the date on which it was finalized—for example, each respective note may indicate the date on which a code was previously saved, submitted to an insurer, or officially recorded for the patient. In certain embodiments, the system has access to a record of previously finalized codes, and retrieves and presents information about the previously finalized codes as coded opportunity notes via a user interface such as 1300, 1500, or 900.

FIG. 15 shows an exemplary user interface 1500 for documenting health services for a patient—specifically, it shows the medical codes that have been associated with a patient during one or more health plan years, and the associated information that may be provided to a risk model to arrive at a RAF (risk adjustment factor) for the patient. User interface 1500 shows the translation of a first type of medical code 1502 (e.g., an ICD code) to a second type of medical code 1504 (e.g., an HCC code) and the associated risk score components 1506 for those particular condition codes. User interface 1500 additionally shows a demographics score component 1507 and an interaction factor component 1508. In certain embodiments, the user interface may show multiple pairs of interacting codes if applicable. In certain embodiments, user interface 1500 will indicate whether a code has been claimed in a particular health plan year.

FIG. 16 shows an exemplary user interface 1600 for documenting health services for a patient—specifically, it shows the activity log for changes made to the medical codes associated with a patient.

Figure 17:
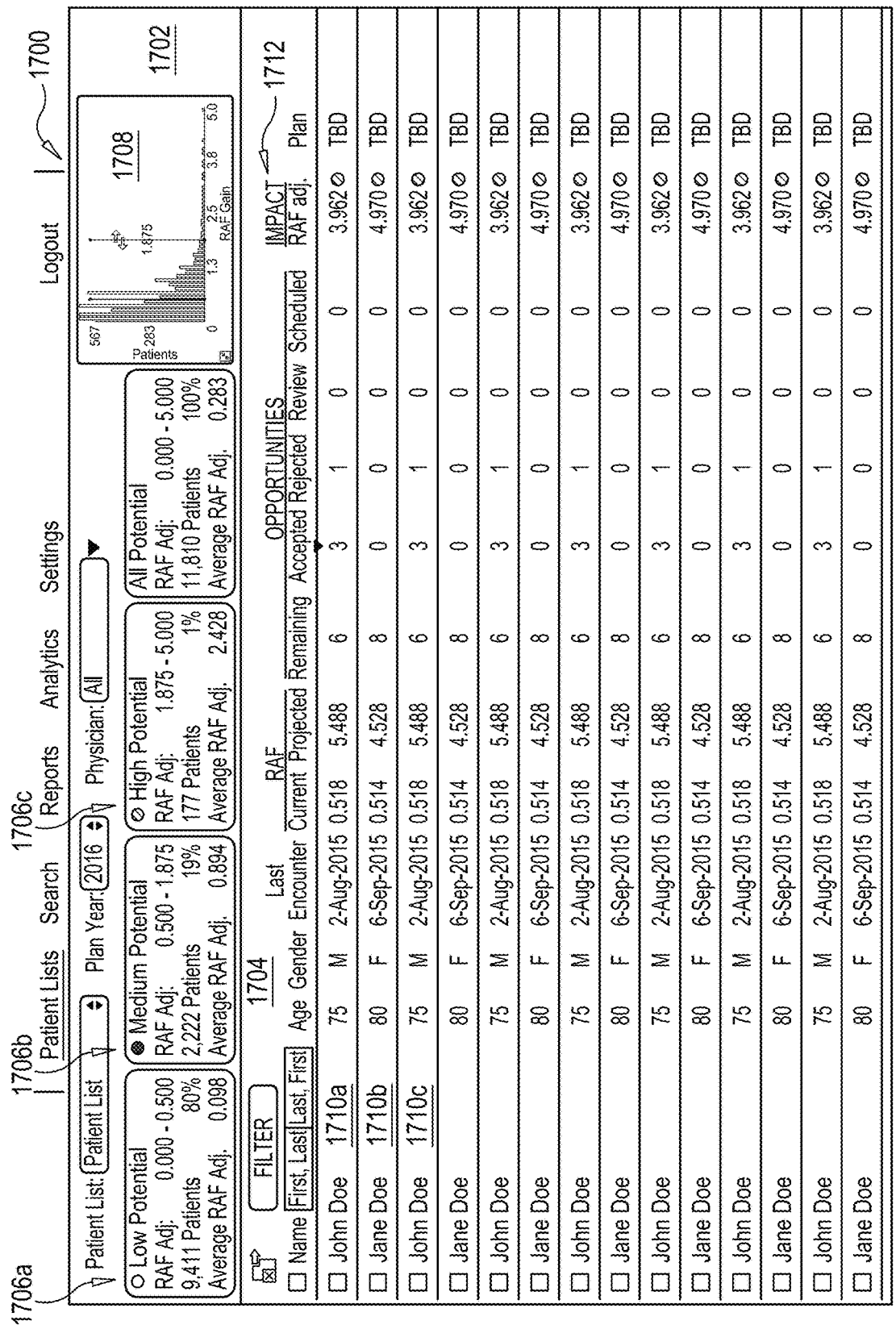
FIG. 17 shows an exemplary user interface concerning documenting health services, consistent with some embodiments of the invention.

FIG. 17 shows an exemplary user interface 1700 concerning documenting health services—specifically, it shows a listing of a population of patients. User interface 1700 includes a panel 1702 providing various filtering options and displaying aggregate features of the population, and a panel 1704, displaying a listing of patients 1710, including, for example, patients 1710a-c. Selection of any patient 1710 may cause the user to be presented with, e.g., user interface 900 or 1300 for interacting with codes associated with that patient. Patients may be grouped into risk stratified cohorts to allow users to view the patient distribution across particular risk-adjusted cohorts, or all together—for example, three categories 1706a-c based on their potential RAF adjustment. Patients associated with high potential RAF adjustments (i.e., category 1706c) may be patients associated with missing or inaccurate medical codes, based on an analysis of patient documents. User interface 1700 permits a user to focus only on a selected category of patients, e.g., the patients in category 1706c. The categories 1706a-c as shown in user interface 1700 are selectable elements; upon selection, only patients associated with a projected RAF adjustment within the category's range will be displayed in panel 1704. Panel 1702 additionally includes a risk stratification histogram 1708 that provides a visual illustration of the number of patients in each category 1706a-c, in which elements of the histogram are displayed or marked according to a particular risk category. The histogram 1708 may be selected and interacted with as explained below in connection with FIG. 19.

The listing of patients in panel 1704 provides an overview of each patient 1710, including the current and projected RAF if all proposed codes are accepted, and the projected RAF adjustment 1712 (i.e., the difference between the projected and current RAF). The listing in panel 1704 may be exported to a tab-separated text file, Excel spreadsheet, or other appropriate format. The listing may be sorted by any column; for example, the listing shown in FIG. 17 is sorted by the number of accepted opportunities (e.g., accepted proposed codes), as indicated by an indicator in the label for that column.

Figure 18:
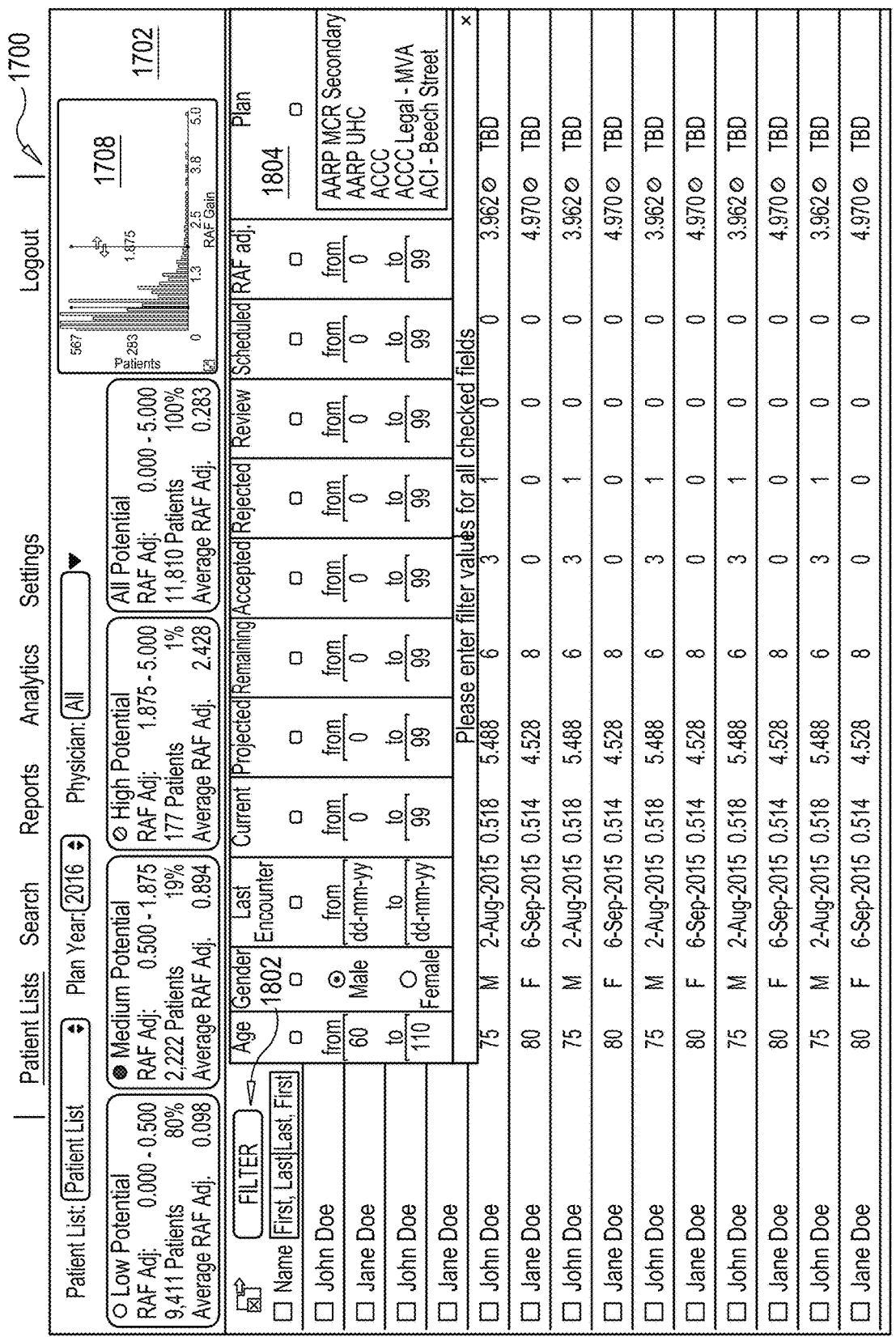
FIG. 18 shows an exemplary user interface concerning documenting health services, consistent with some embodiments of the invention.

FIG. 18 shows another view of exemplary user interface 1700 showing a listing of patients. Selection of filter control 1802 causes window 1804 to be presented, providing a selection of filtering options based on, for example, age, gender, date of last encounter (i.e., office visit or laboratory report date), current RAF, projected RAF, remaining/accepted/rejected/marked-for-review/scheduled opportunities, RAF adjustment, and health plan.

Figure 19:
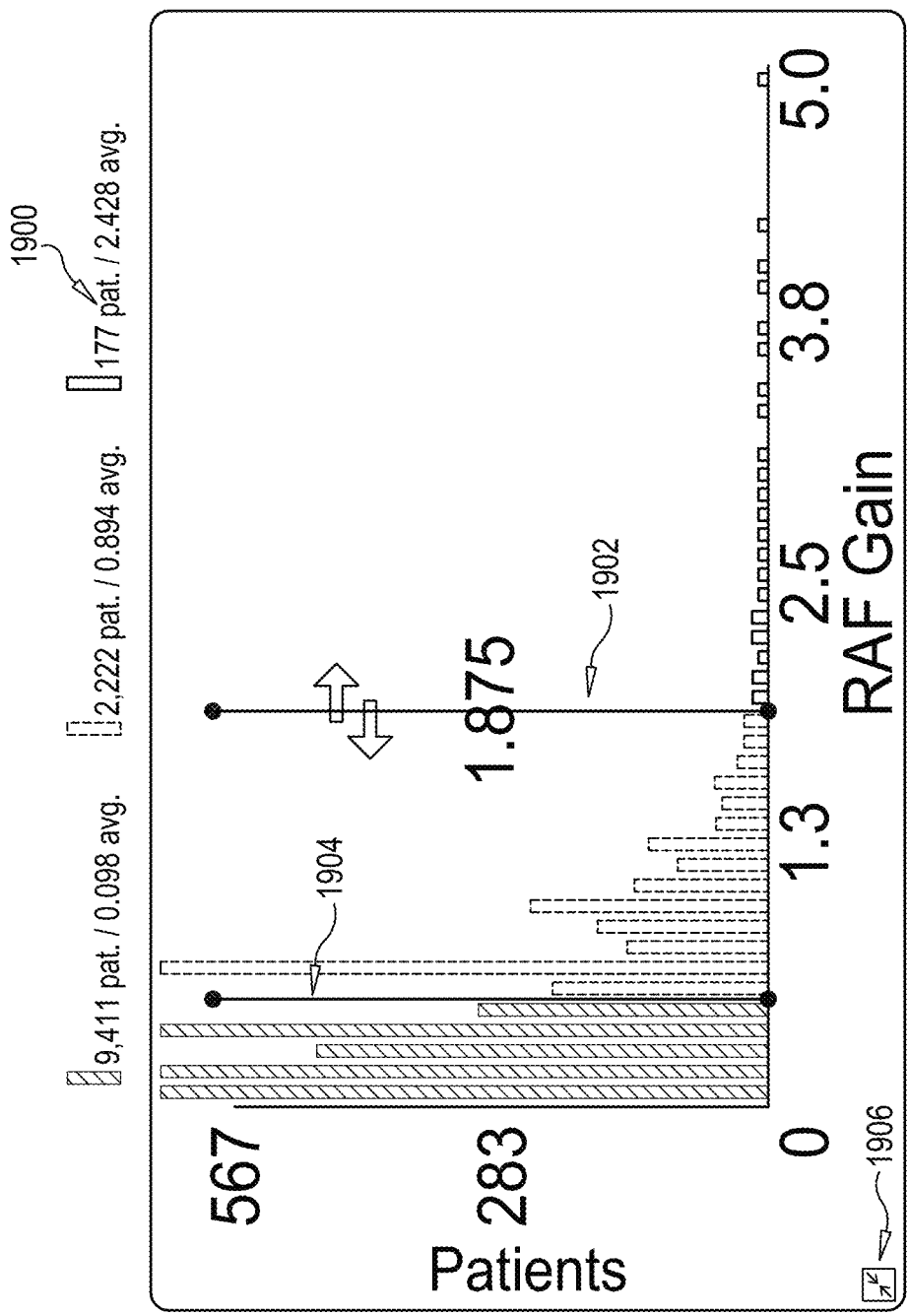
FIG. 19 shows an exemplary user interface concerning documenting health services, consistent with some embodiments of the invention.

FIG. 19 shows an exemplary user interface concerning documenting health services—specifically, it shows a user interface 1900 that may be provided upon selecting histogram 1708 in user interface 1700. User interface 1900 permits the user to adjust the bounds of the three categories of patients based on their potential RAF adjustment. For example, the user may select and drag bound 1902 demarking the boundary between the medium and high potential RAF adjustment category to change the threshold potential RAF adjustment for membership in a category. In certain embodiments, as the bounds 1902 and 1904 are shifted, the bars of the histogram are automatically recolored (or otherwise redrawn) to indicate their group membership, and the current potential RAF gain measure threshold is indicated to the user (e.g., 1.875 as shown in FIG. 19). In certain embodiments, the number of patients in each category and the average potential RAF gain measure for each category is provided and updated as the bounds are moved. In user interface 1900, element 1906 may be selected to accept any changes to the category bounds and cause the patient listing in user interface 1700 to update accordingly.

Figure 21:
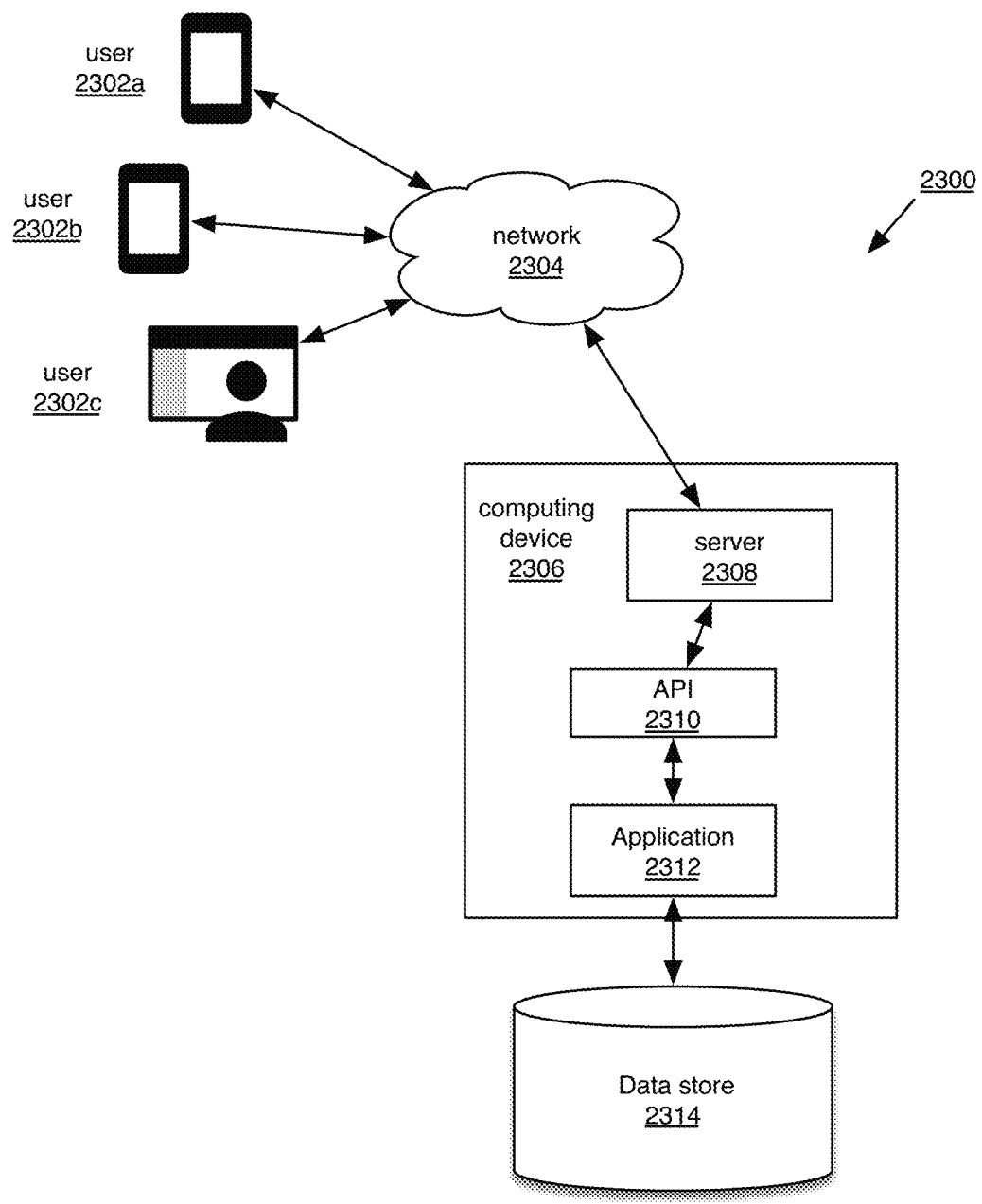
FIG. 21 is a block diagram showing exemplary data flows for an exemplary system, consistent with some embodiments of the invention.

FIG. 21 is a block diagram showing exemplary data flows for an exemplary system 2300. In certain embodiments, users access the system via one or more computing devices such as devices 2302a-c. User devices 2302a and 2302b may include mobile devices such as a tablet or smart phone. User device 2302c may include a laptop or desktop computer. In certain embodiments, the user devices may provide data to one or more computing devices 2306 via network 2304. Network 2304 may include, for example, a LAN, wired or wireless network, private or public network, telecommunications network, or the internet.

In certain embodiments, one or more computing devices 2306 host a server 2308, such as an HTTP server, and an application 2312 that implements aspects of the data engine 106. Knowledgebases such as a code translation knowledgebase or other databases may be stored in data store 2314. Application 2312 may support an Application Programming Interface (API) 2310 providing external access to methods for accessing data store 2314. In certain embodiments, client applications running on user devices 2302 may access API 2310 via server 2308 using protocols such as HTTP or FTP.

Below are set out hardware (e.g., machine) and software architectures that may be deployed in the systems described above, in various example embodiments.

Figure 22:
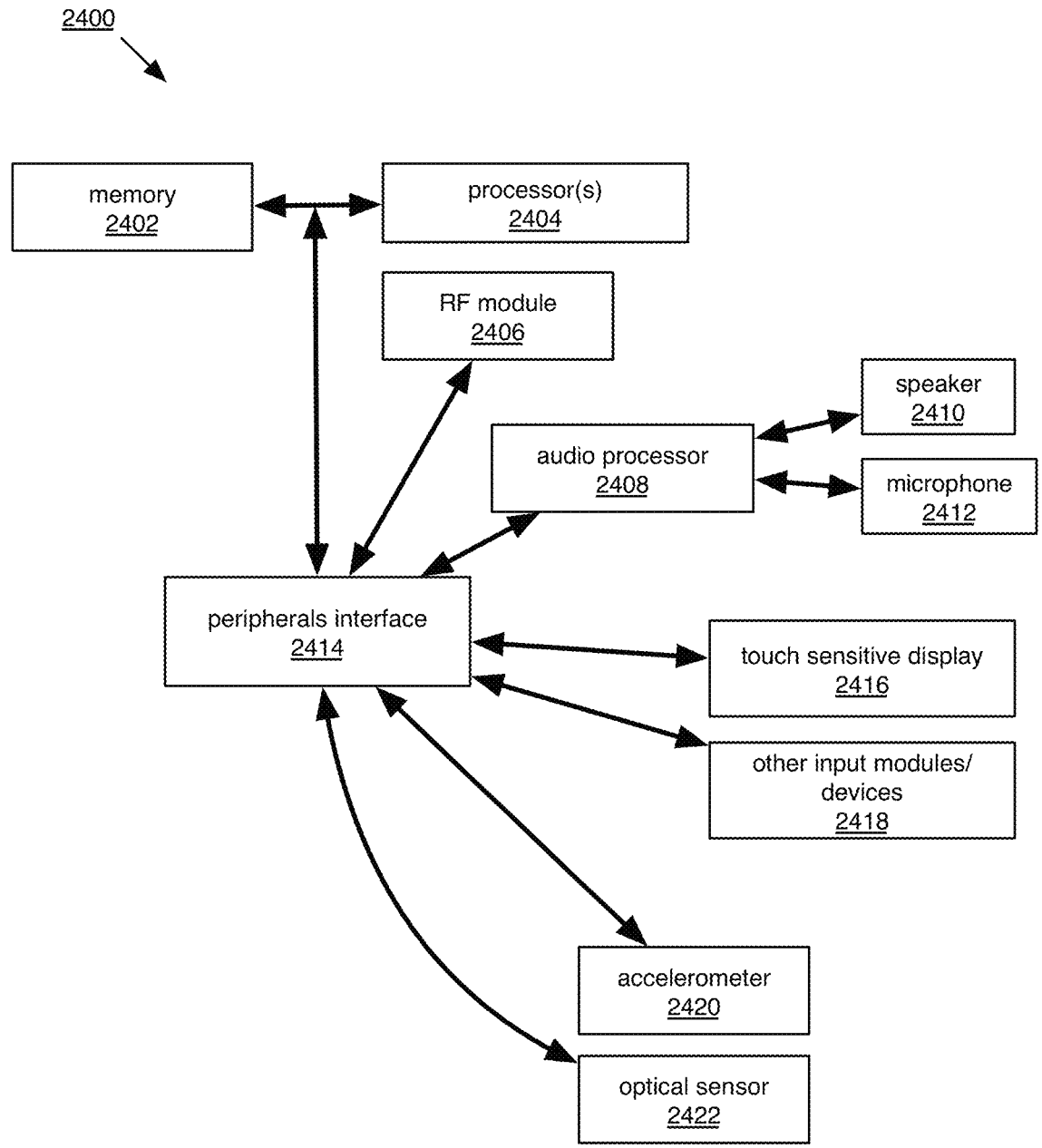
FIG. 22 is a block diagram showing an exemplary mobile computing device, consistent with some embodiments of the invention.

FIG. 22 is a block diagram showing an exemplary mobile computing device 2400. The device 2400 may have a memory 2402 which may include one or more types of computer readable medium, such as RAM, optical storage devices, or flash memory. Memory 2402 may store an operating system, applications, and communication procedures. Device 2400 may include one or more data processors, image processors, or central processing units 2404. Device 2400 may include peripherals interface 2414 coupled to RF module 2406, audio processor 2408, touch sensitive display 2416, other input modules/devices 2418, accelerometer 2420 and optical sensor 2422.

RF module 2406 may include a cellular radio, Bluetooth radio, NFC radio, WLAN radio, GPS receiver, and antennas used by each for communicating data over various networks, such as a telecommunications network.

Audio processor 2408 may be coupled to a speaker 2410 and microphone 2412. Touch sensitive display 2416 receives touch-based input. Other input modules or devices 1018 may include, for example, a stylus, voice recognition via microphone 2412, or an external keyboard.

Accelerometer 2420 may be capable of detecting changes in orientation of the device, or movements due to the gait of a user. Optical sensor 2422 may sense ambient light conditions, and acquire still images and video.

Figure 23:
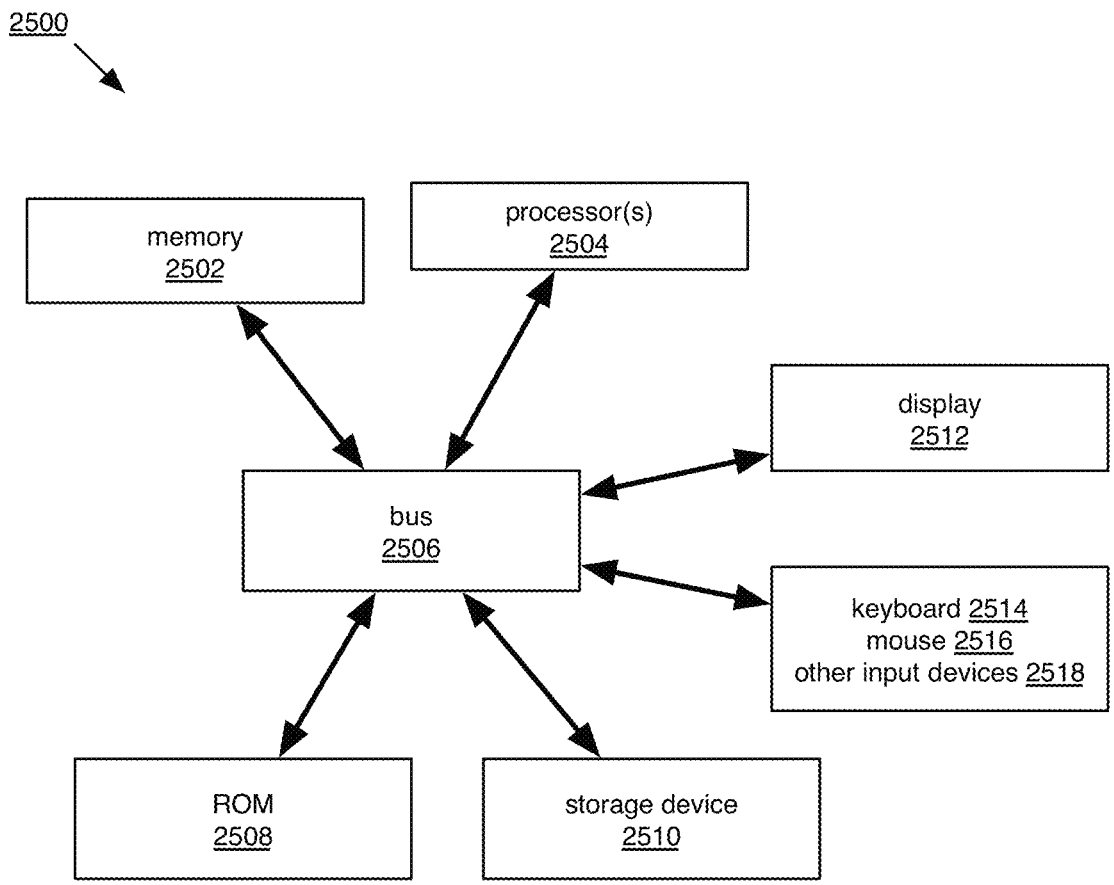
FIG. 23 is a block diagram showing an exemplary computing device, consistent with some embodiments of the invention.

FIG. 23 is a block diagram showing an exemplary computing system 2500 that is representative any of the computer systems or electronic devices discussed herein. Note that not all of the various computer systems have all of the features of system 2500. For example, systems may not include a display inasmuch as the display function may be provided by a client computer communicatively coupled to the computer system or a display function may be unnecessary.

System 2500 includes a bus 2506 or other communication mechanism for communicating information, and a processor 2504 coupled with the bus 2506 for processing information. Computer system 2500 also includes a main memory 2502, such as a random access memory or other dynamic storage device, coupled to the bus 2506 for storing information and instructions to be executed by processor 2504. Main memory 2502 also may be used for storing temporary variables or other intermediate information during execution of instructions to be executed by processor 2504.

System 2500 includes a read only memory 2508 or other static storage device coupled to the bus 2506 for storing static information and instructions for the processor 2504. A storage device 2510, which may be one or more of a hard disk, flash memory-based storage medium, magnetic tape or other magnetic storage medium, a compact disc (CD)-ROM, a digital versatile disk (DVD)-ROM, or other optical storage medium, or any other storage medium from which processor 2504 can read, is provided and coupled to the bus 2506 for storing information and instructions (e.g., operating systems, applications programs and the like).

Computer system 2500 may be coupled via the bus 2506 to a display 2512 for displaying information to a computer user. An input device such as keyboard 2514, mouse 2516, or other input devices 2518 may be coupled to the bus 2506 for communicating information and command selections to the processor 2504.

The processes referred to herein may be implemented by processor 2504 executing appropriate sequences of computer-readable instructions contained in main memory 2504. Such instructions may be read into main memory 2502 from another computer-readable medium, such as storage device 2510, and execution of the sequences of instructions contained in the main memory 2502 causes the processor 2504 to perform the associated actions. In alternative embodiments, hard-wired circuitry or firmware-controlled processing units (e.g., field programmable gate arrays) may be used in place of or in combination with processor 2504 and its associated computer software instructions to implement the invention. The computer-readable instructions may be rendered in any computer language including, without limitation, Python, Objective C, C#, C/C++, Java, Javascript, assembly language, markup languages (e.g., HTML, XML), and the like. In general, all of the aforementioned terms are meant to encompass any series of logical steps performed in a sequence to accomplish a given purpose, which is the hallmark of any computer-executable application. Unless specifically stated otherwise, it should be appreciated that throughout the description of the present invention, use of terms such as "processing", "computing", "calculating", "determining", "displaying", "receiving", "transmitting" or the like, refer to the action and processes of an appropriately programmed computer system, such as computer system 2500 or similar electronic computing device, that manipulates and transforms data represented as physical (electronic) quantities within its registers and memories into other data similarly represented as physical quantities within its memories or registers or other such information storage, transmission or display devices.

Figure 24:
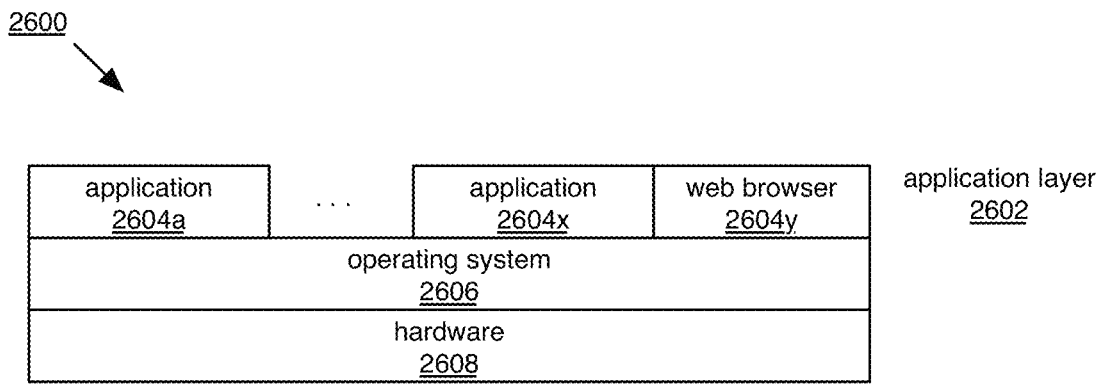
FIG. 24 is a block diagram showing an exemplary computing system, consistent with some embodiments of the invention.

FIG. 24 illustrates a computer system 2600 from the point of view of its software architecture. Computer system 2600 may be any of the electronic devices or, with appropriate applications comprising a software application layer 2602, may be a computer system for use with the services described herein. The various hardware components of computer system 2600 are represented as a hardware layer 2608. An operating system 2606 abstracts the hardware layer and acts as a host for various applications 2604, that run on computer system 2600. The operating system may host a web browser application 2604$y$, which may provide access for the user interfaces, etc.

The foregoing description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," and the like are used merely as labels, and are not intended to impose numerical requirements on their objects.

What is claimed is:

1. A method comprising:
   at a server, preprocessing one or more patient documents to create a plurality of segments of the document at varying levels of granularity;
   at a server, enriching the one or more patient documents by:
      generating entity links between supporting evidence in the one or more patient documents and entities that are concepts in a semantic taxonomy having a graphical structure of related concepts by, for each respective document:
         scoring a plurality of candidate entity links with a concept score, each link comprising a specification of a concept and one or more segments, wherein the concept score is based on (1) an occurrence score based on the number of occurrences of instances of a first concept in the respective document, and (2) a relationship score based on instances of additional concepts in the respective document that are not the first concept, wherein the additional concepts are each connected to the first concept in the graphical structure of related concepts; and
         retaining the respective candidate entity links as entity links if the concept score is greater than a threshold;
      correcting the one or more entity links using a word-sense disambiguation annotator by evaluating the relatedness of the respective segments to a library of homonyms and collections of words associated with respective members of homonym pairs, and removing respective entity link associations with concepts, terms, and/or extracted health data corresponding to a respective member if the relatedness of a respective segment to a respective collection of words is low, and adding additional entity link associations with concepts, terms, and/or extracted health data corresponding to the respective member if the relatedness to a respective collection of words is high; and
      correcting the one or more entity links using a coordinate-expansion annotator by:
         identifying conjunctions in the respective segments and creating separated terms based on the segments;
         evaluating whether additional instances of entities exist in the segments by parsing the separated terms of the segments; and
         generating additional entity links accordingly; and
   at a server, generating a search index for the one or more patient documents based on the one or more entity links.

2. The method of claim 1, wherein enriching the one or more patient documents further comprises:

generating entity links between supporting evidence in the one or more patient documents and entries in a customer-specific dictionary or a molecule database, by creating a respective entity link comprising a specification of a term, a term type, and one or more segments that satisfy a dictionary relationship rule, wherein the dictionary relationship rule is based on whether a respective entry is the same as a term in a respective segment.

3. The method of claim 1, wherein one or more concepts of the semantic taxonomy have a synonyms attribute.

4. The method of claim 1, wherein at least one entity link specifies segments located in two or more patient documents.

5. The method of claim 1, further comprising:
for each of one or more entity links, inserting tags referencing entity link information around the associated segments in a markup language version of the one or more patient documents.

6. The method of claim 1, wherein enriching the one or more patient documents further comprises:
generating entity links between supporting evidence in the one or more patient documents and terms in a dictionary by creating a respective entity link comprising a specification of a term, a term type, and one or more segments that satisfy a dictionary relationship rule, wherein the dictionary relationship rule is based on whether a respective term is the same as a term in a respective segment.

7. The method of claim 1, wherein the occurrence score depends upon how often the concept occurs in a title, keywords, abstract, or body of the respective document.

8. The method of claim 1, wherein whether an instance of a concept occurs in the respective document is based on whether an attribute of the concept is the same or similar to text in one or more segments of the respective document.

9. The method of claim 1, wherein the relationship score is based on additional concepts that are each connected to the first concept in the semantic taxonomy with an edge distance of one.

10. The method of claim 1, wherein the relationship score is based on additional concepts that have a positive relationship to the first concept.

11. The method of claim 1, further comprising:
generating care plan information based on the one or more entity links, wherein the one or more patient documents are associated with a patient, and the one or more entity links include health conditions and socioeconomic data for the patient.

12. The method of claim 1, further comprising:
identifying a plurality of entity link concepts as RAF concepts, wherein RAF concepts are concepts that affect a risk adjustment factor (RAF) determination;
generating one or more RAF scores for a patient associated with the patient documents based on one or more subsets of the plurality of entity link concepts.

13. A method comprising:
at a server, preprocessing one or more patient documents to create a plurality of segments of the document at varying levels of granularity;
at a server, enriching the one or more patient documents by:
generating entity links between supporting evidence in the one or more patient documents and entities that are concepts, terms, and/or extracted health data using a stack of annotators, wherein the respective entity links comprise a specification of a value, a value type, and one or more segments, by:
generating one or more document-section-specific entity links using a document-section-specific annotator by:
generating one or more semantic-type entity links using a semantic-type annotator by:
generating one or more base-term-type entity links using a base-term-type annotator; and
based on the presence of semantic elements of a semantic-type rule, wherein one or more of the semantic elements were generated as components of base-term-type entity links, evaluating the semantic-type rule, wherein the semantic-type rule evaluates vital signs or observations, laboratory tests or laboratory results, drugs or dosages, conditions, or treatment procedures; and
associating the results of the semantic-type rule as semantic-type entity links; and
based on the presence of section-specific elements of a document-section-specific rule, wherein one or more of the section-specific elements were generated as components of base-term-type entity links or semantic-type entity links, evaluating the document-section-specific rule; and
associating the results of the document-section-specific rule as document-section-specific entity links;
correcting the one or more entity links using a word-sense disambiguation annotator by evaluating the relatedness of the respective segments to a library of homonyms and collections of words associated with respective members of homonym pairs, and removing respective entity link associations with concepts, terms, and/or extracted health data corresponding to a respective member if the relatedness of a respective segment to a respective collection of words is low, and adding additional entity link associations with concepts, terms, and/or extracted health data corresponding to the respective member if the relatedness to a respective collection of words is high; and
correcting the one or more entity links using a coordinate-expansion annotator by:
identifying conjunctions in the respective segments and creating separated terms based on the segments;
evaluating whether additional instances of entities exist in the segments by parsing the separated terms of the segments; and
generating additional entity links accordingly; and
at a server, generating a search index for the one or more patient documents based on the one or more entity links.

14. The method of claim 13, wherein the semantic-type rule comprises matching a pattern in a respective segment using a regular expression.

15. The method of claim 13, wherein the semantic-type rule comprises a machine-readable clinical guideline.

16. The method of claim 13, wherein the base-term-type annotator creates base-term-type entity links that identify negation of a term in a segment.

17. The method of claim 13, wherein the base-term-type annotator creates base-term-type entity links that identify ages, gender, and geography.

18. The method of claim 13, wherein the base-term-type annotator creates base-term-type entity links that identify temporal values.

19. The method of claim 13, wherein enriching the one or more patient documents further comprises:
generating entity links between supporting evidence in the one or more patient documents and entries in a customer-specific dictionary or a molecule database, by creating a respective entity link comprising a specification of a term, a term type, and one or more segments that satisfy a dictionary relationship rule, wherein the dictionary relationship rule is based on whether a respective entry is the same as a term in a respective segment.

20. The method of claim 13, wherein at least one entity link specifies segments located in two or more patient documents.

21. The method of claim 13, further comprising:
for each of one or more entity links, inserting tags referencing entity link information around the associated segments in a markup language version of the one or more patient documents.

* * * * *